US007037693B2

(12) United States Patent
Brash et al.

(10) Patent No.: US 7,037,693 B2
(45) Date of Patent: May 2, 2006

(54) **MUSKMELON (*CUCUMIS MELO*) HYDROPEROXIDE LYASE AND USES THEREOF**

(75) Inventors: Alan Brash, Brentwood, TN (US); Nathalie Tijet, Tucson, AZ (US); Ian M. Whitehead, Singapore (SG)

(73) Assignees: Vanderbilt University, Nashville, TN (US); Firmenich SA, Geneva (CH)

( * ) Notice: Subject to any disclaimer, the term of this patent is extended or adjusted under 35 U.S.C. 154(b) by 670 days.

(21) Appl. No.: 09/884,260

(22) Filed: Jun. 19, 2001

(65) Prior Publication Data

US 2002/0098570 A1 Jul. 25, 2002

Related U.S. Application Data

(63) Continuation of application No. 09/537,357, filed on Mar. 29, 2000, now Pat. No. 6,271,018.

(51) Int. Cl.
*C12P 7/24* (2006.01)

(52) U.S. Cl. ........................ 435/147; 435/155; 435/232

(58) Field of Classification Search ................ 435/232, 435/132, 147, 155; 536/23.2
See application file for complete search history.

(56) References Cited

U.S. PATENT DOCUMENTS 5,464,761 A 11/1995 Muller et al. ............... 435/147
6,200,794 B1 3/2001 Whitehead et al. ......... 435/232

FOREIGN PATENT DOCUMENTS

EP 0801133 A2 10/1997
WO WO9958648 A 11/1999
WO WO00/00627 1/2000

OTHER PUBLICATIONS

Fauconnier, M.L., Perez, A.G., Sanz, C., Marlier, M. (1997). Purification and Characterization of Tomato Leaf (*Lycopersicon esculentum* Mill.) Hydroperoxide Lyase. *J. Agric. Food Chem.* 45(11):4232-4236.

Matsui K., Shibata Y., Kajiwara, T. and Hatanaka A. (1989). Separation of 13 and 9-hydroperoxide lyase activities in cotyledons of cucumber seedlings. *Z. Naturforsch.* 44c:883-885.

(Continued)

*Primary Examiner*—Nashaat T. Nashed
(74) *Attorney, Agent, or Firm*—Needle & ROsenberg, PC

(57) ABSTRACT

The present invention provides a fatty acid lyase, wherein the activity of the lyase for 9-hydroperoxide substrates is greater than the activity for 13-hydroperoxide substrates and wherein $K_m$ and $V_{max}$ of the lyase for 9-hydroperoxylinolenic acid are greater than $K_m$ and $V_{max}$ of the lyase for 9-hydroperoxylinoleic acid. More particularly, the invention provides a lyase present in melon (*Cucumis melo*). The invention also provides a nucleic acid encoding the lyase, vectors, and expression systems with which the recombinant lyase can be obtained. The invention also provides methods of using the lyase of the invention, including methods of cleaving 9-hydroperoxylinoleic acid, 9-hydroperoxylinolenic acid, 13-hydroperoxylinoleic acid, and 13-hydroperoxylinolenic acid. Also, the invention provides a method of preparing 3-(Z)-nonenal, (3Z,6Z)-nonadienal, 2-(E)-nonenal, (2E,6Z)-nonadienal, or their corresponding alcohols and a method of preparing n-hexanal, 3-(Z)-hexen-1-al, 2-(E)-hexen-1-al, or their corresponding alcohols using the lyase of the present invention.

20 Claims, 13 Drawing Sheets

```
    ---------------------------------------- Majority
             10        20        30        40

1   MASSALNNLVAVNPNTLSPSPKSTPLPNTFSNLRRVSAFR AOS-Flax
1   ---------------------------------------- AOS-Guyaule
1   ------------------MASISTPFPISLHPKTVRSKPL AOS-Arabi
1   ----MSSIVIPSLQPHLRFPSSQETPQRSRSRVGFVSIRP AOS-Melon
1   --------------------------------------MA HPL-Guava
1   ---------------------------------------- HPL-Banana
1   ---------------------------------------- HPL-Pepper
1   ---------------------------------------- HPL-Melon

    --------------P-MSLSPASSSDPTTLPLRKIPGSYG Majority
             50        60        70        80

410 PIKASLFGDSPIKIPGITSQPPPSSDETTLPIRQIPGDYG AOS-Flax
1   ------------------------MDPSSKPLREIPGSYG AOS-Guayule
23  KFRVLTRPIKASGSETPDLTVATRTGSKDLPIRNIPGNYG AOS-Arabi
37  IYATDGVSSSSSSSLQVPQRIVSPPEPTKLPLRKVPGDYG AOS-Melon
3   RVVMSNMSPAMSSTYPPSLSPPSSPRPTTLPVRTIPGSYG HPL-Guava
1   --------------MAMMWSSASATAVTTIPTRPIPGSYG HPL-Banana
1   ------------MIPIMSSAPLSTATPISLPVRKIPGSYG HPL-Pepper
1   -------------------MATPSSSSPELPLKPIPGGYG HPL-Melon
```

OTHER PUBLICATIONS

Matsui K, Toyota H., Kajiwara T., Kakuno T. and Hatanaka A. (1991). Fatty acid hydroperoxide cleaving enzyme, hydroperoxide lyase, from tea leaves. *Phytochemistry* 30(7): 2109-2113.

Matsui K., Shibutani M., Hase T., and Kajiwara T. (1996). Bell Pepper Fruit Fatty Acid Hydroperoxide Lyase is a Cytochrome P-450 (CYP74B). *FEBS Lett.* 394:21-24.

Olias J.M., Rios J.J., Valle M., Zamora R., Sanz L.C. and Axelrod B. (1990). Fatty acid hydroperoxide lyase in germinating soybean seedlings. *J. Agric. Food Chem.* 38: 624-630.

Schreier P. and Lorenz G. (1982). Separation, partial purification and characterization of a fatty acid hydroperoxide cleaving enzyme from apple and tomato fruits. *Z. Naturforsch.* 37c:165-173.

Shibata Y., Matsui K., Kajiwara T. and Hatanaka, A. (1995). Purification and properties of fatty acid hydroperoxide lyase from green bell pepper fruits. *Plant Cell Physiology* 36(1): 147-156.

Tressl, R. and Drawert, F. (1973). Biogenesis of banana volatiles. *J. Agric. Food Chem.* 21(4):560-565.

Vick B.A. and Zimmerman D.C. (1976). Lipoxygenase and hydroperoxide lyase in germinating watermelon seedlings. *Plant Physiol.* 57:780-788.

Noordermeer, M. A., Veldink, G. A., Vliegenthart, J. (1999). Alfalfa contains substantial 9-hydroperoxide lease activity and a 3Z:2E-enal isomerase. *FEBS LETT.* 443:201-204.

J. Rudinger (1976). Characteristics of the amino acids as components of a peptide hormone sequence. In: Peptide Hormes. Ed. J. A. Parsons. University Park Press, Baltimore, MD pp. 1-7.

Ngo et al. (1994). Computational complexity, protein structure prediction, and the ILevinthal paradox. In: The Protein Folding Problem and Tertiary Structure Prediction. Eds. Merz et al. Birkhauser et al. Boston, MA pp. 491-495.

Thornton et al. (1995). Protein Engineering: Editorial Overview. Current Opinion in Biotechnology 6(4):367-369.

Wallace (1993), Understanding cytochrome c funtion: engineering protein structure by semisynthesis. The FASEB Journal 7:505-515.

Hornostaj and Robinson (1999), Purification of hydroperoxide lease from cucumbers. *Food Chemistry* 66: 173-180.

Itoh and Vick (1999). The purification and characterization of fatty acid hydroperoxide lease in sunflower. *Biochim. Biophys. Acta* 1436:531-540.

Kim and Gosch (1981). Partial Purification and Properties of a Hydroperoxide Lyase from Fruits of Pear. *J. Agri. Food Chem.* 29:1220-1225.

```
       LPLLGPIKDRLDYFYFQG-REEFFRSRIEKYNSTVFRANM Majority
                 90        100       110       120

 81    LPGIGPIQDRLDYFYNQG-REEFFKSRLQKYKSTVYRANM AOS-Flax
 17    IPFFQPIKDRLEYFYGTGGRDEYFRSRMQKYQSTVFRANM AOS-Guayule
 63    LPIVGPIKDRWDYFYDQGA-EEFFKSRIRKYNSTVYRVNM AOS-Arabi
 77    PPMFGALKDRHDYFYNQG-REEYLKSRMLRYESTVYRTNM AOS-Melon
 43    WPLLGPISDRLDYFWFQG-PETFFRKRIEKYKSTVFRANV HPL-Guava
 27    PPLVGPLKDRLDYFWFQG-PETFFRSRMATHKSTVFRTNM HPL-Banana
 29    FPLLGPLWDRLDYNWFQK-LPDFFSKRVEKYNSTVFRTNV HPL-Pepper
 22    FPFLGPIKDRYDYFYFQG-RDEFFRSRITKYNSTVFRANM HPL-Melon

       PP--GPFIGSNPRVVVLLDAKSFPVLFDMSKVEKKDLLTG Majority
                130       140       150       160

120    PP--GPFIASNPRVIVLLDAKSFPVLFDMSKVEKKDLFTG AOS-Flax
 57    PP--GPFVSSNPKVIVLLDAKSFPILFDVSKVEKKDLFTG AOS-Guayule
102    PP--GAFIAENPQVVALLDGKSFPVLFDVDKVEKKDLFTG AOS-Arabi
116    PP--GPFITSDSRVVVLLDGKSFPVLFDHSKVEKKDLFTG AOS-Melon
 82    PPCFPFFSNVNPNVVVVLDCESFAHLFDMEIVEKSNVLVG HPL-Guava
 66    PPTFPFFVGVDPRVVTVLDCTSFSALFDLEVVEKKNILIG HPL-Banana
 68    PPCFPFFLGVNPNVVAVLDVKSFAHLFDMEIVEKANVLVG HPL-Pepper
 61    PP--GPFISSDSRVVVLLDALSFPILFDTAKVEKRNILDG HPL-Melon
```

FIG. 1B

```
    T Y M P S T E L T G G Y R V L S Y L D P S E P D H A Q L K N L L F F L L K R S S  Majority
                      170                           180                           190                           200
158 T Y M P S T E L T G G Y R I L S Y L D P S E P N H T K L K Q L L F N L I K N R R  AOS-Flax
95  T Y M P S T K L T G A Y R V L S Y L D P S E P R H A Q L K N L L F F M L K N S S  AOS-Guayule
140 T Y M P S T E L T G G Y R I L S Y L D P S E P K H E K L K N L L F F L L K S S R  AOS-Arabi
154 T Y M P V T E L T G G Y R V L S Y I D P S E P D H A K L K Q L I F F L L K H R R  AOS-Melon
122 D F M P S V K Y T G N I R V C A Y L D T S E P Q H A Q V K N F A M D I L K R S S  HPL-Guava
106 D Y M P S L S F T G D T R V V V Y L D P S E P D H A R V K S F C L E L L R R G A  HPL-Banana
108 D F M P S V V Y T G D M R V C A Y L D T S E P K H T Q I K N F S L D I L K R S S  HPL-Pepper
99  T Y M P S L S F T G N I R T C A Y L D P S E T E H S V L K R L F L S F L A S R H  HPL-Melon

    D R W I P E F X S T L S E L F E T L E S D L A K D G K - A A F N A L - E Q A A F  Majority
                      210                           220                           230                           240
198 D Y V I P E F S S S F T D L C E V V E Y D L A T K G K - A A F N D P A E Q A A F  AOS-Flax
135 N R V I P Q F E T T Y T E L F E G L E A E L A K N G K - A A F N D V G E Q A A F  AOS-Guayule
180 N R I F P E F Q A T Y S E L F D S L E K E A F P L R E - S G F R R F Q R R N R L  AOS-Arabi
194 D K I M P E F H S T F S E L F E T L E K D L A A A G R - A E Y N A S G E Q A A F  AOS-Melon
162 K V W E S E V I S N L D T M W D T I E S S L A K D G N A S V I F P L - Q K F L F  HPL-Guava
146 K T W V S S F L S N L D V M L A T I E Q G I A K D G S A G L F G P L - Q K C I F  HPL-Banana
148 K T W V P T L V K E L D T L F G T F E S D L S K S K S A S L L P A L - Q K F L F  HPL-Pepper
139 D R F I P L F R S S L S E M F V K L E D K L S E K K I A D F N S I - S D S M S  HPL-Melon
```

FIG. 1C

```
    NFLSRSFLGADPSDSK-LGASGPGLIDKWVLFQLAPTLSI Majority
             250       260       270       280

237 NFLSRAFFGVKPIDTP-LGKDAPSLISKWVLFNLAPILSV AOS-Flax
174 RFLGRAYFNSNPEETK-LGTSAPTLISSWVLFNLAPTLDL AOS-Guayule
219 LFLGSSFLRDESRRYK-LKADAPGLITKWVLFNLHPLLSI AOS-Arabi
233 NFLARSLFGADPVDSK-LGRDAPKLIAKWVLFQLGPVLSL AOS-Melon
201 NFLSKSIIGADPAASPQVAKSGYAMLDRWLALQLLPTINI HPL-Guava
185 AFLCKSIIGADPSVSPDVGENGFVMLDKWLALQLLPTVKV HPL-Banana
187 NFFSLTFLGADPSASPEIANSGFAYLDAWLAIQLAPTVSI HPL-Pepper
178 FDYVFRLLSDGTPDSK-LAAEGPGMFDLWLVFQLAPLASI HPL-Melon

    GLPKVV---EEILLHSFRLPFFLVKSDYRKLYEFFESSAG Majority
             290       300       310       320

276 GLPKEV---EEATLHSVRLPPLLVQNDYHRLYEFFTSAAG AOS-Flax
213 GLPWFL---QEPLLHTFRLPAFLIKSTYNKLYDYFQSVAT AOS-Guayule
258 GLPRVI---EEPLIHTFSLPPALVKSDYQRLYEFL-RIRG AOS-Arabi
272 GLPKVV---EELLLRTVRLPPALIKADYRRLYDFFYKSSE AOS-Melon
241 GV--L-QPLVEIFLHSWAYPFALVSGDYNKLYQFIEKEGR HPL-Guava
225 GA--IPQPLEEILLHSFPLPFFLVSRDYRKLYEFVEKQGQ HPL-Banana
227 GV--L-QPLEEIFVHSFSYPYFLVRGGYEKLIKFVKSEAK HPL-Pepper
217 GLPKIFSVFEDLVIHTIPLPFFPVKSGYRKLYEAFYSSSG HPL-Melon
```

FIG.1D

```
     E V L E E A E - K L G I S R E E A I H N L L F A L G F N A F G G F K I L F P T L  Majority
                   330                 340                 350                 360
313  S V L D E A E - Q S G I S R D E A C H N I L F A V C F N S W G G F K I L F P S L  AOS-Flax
250  P V M E Q A E - K L G V P K D E A V H N I L F A V C F N T F G G V K I L F P N T  AOS-Guayule
294  E I L V E A D - K L G I S R E E A T H N L L F A T S F N T W G G M K I L F P N M  AOS-Arabi
309  A V F E E A D - R L G I S R E E A C H N L L F T T C F N S F G G M K I F F P N M  AOS-Melon
278  E A V E R A K A E F G L T H Q E A I H N L L F I L G F N A F G G F S I F L P T L  HPL-Guava
263  E V V R R A E T E H G L S K H D A I N N I L F V L G F N A F G G F S V F F P T L  HPL-Banana
264  E V L T R A Q T D F Q L T E Q E A I H N L L F I L G F N A F G G F T I F L P T L  HPL-Pepper
257  S F L D E A E - K Q G I D R E K A C H N L V F L A G F N A Y G G M K V L F P T L  HPL-Melon

     L K W I G R A - G G - L H T K L A E E V R S A V K S T G - G N L T F E A V E E M  Majority
                   370                 380                 390                 400
352  M K W I G R A - G L E L H T K L A Q E I R S A I Q S T G G G K V T M A A M E Q M  AOS-Flax
289  L K W I G V A - G E N L H T Q L A E E I R G A I K S Y G D G N V T L E A I E Q M  AOS-Guayule
333  V K R I G P G - G H Q V H N R L A E E I R S V I K S N G - G E L T M G A I E K M  AOS-Arabi
348  I K W I G R A - G V N L H T R L A R E I R T A V K A N G - G K I T M G A M E Q M  AOS-Melon
318  L S N I L S D T T G - L Q D R L R K E V R A K G - G P A - - - L S F A S V K E M  HPL-Guava
303  L T T I G R D K T G - L R E K L K D E V R R V M K S R G E K R P S F E T V R E M  HPL-Banana
304  L G N L G D E K N A E M Q E K L R K E V R E K V - G T N Q E N L S F E S V K E M  HPL-Pepper
296  L K W V G T A G E D - L H R K L A E E V R T T V K E E G - - G L T F S A L E K M  HPL-Melon
```

FIG. 1E

```
    ELVKSVVYEALRIEPPVPLQYGRAKKDFVLESHDAAFEVK Majority
             410       420       430       440
391 PLMKSVVYETLRIEPPVALQYGKAKKDFILESHEAAYQVK AOS-Flax
328 PLTKSVVYESLRIEPPVPPQYGKAKSNFTIESHDATFEVK AOS-Guayule
371 ELTKSVVYECLRFEPPVTAQYGRAKKDLVIESHDAAFKVK AOS-Arabi
386 PLMKSVVYEALRIEPPVPVQYGRAKKDLVVESHDAAFEIK AOS-Melon
353 ELVKSVVYETLRLNPPVPFQYARARKDFQLKSHDSVFDVK HPL-Guava
342 ELVRSTVYEVLRLNPPVPLQYGRARTDFTLNSHDAAFKVE HPL-Banana
343 ELVQSFVYESLRLSPPVPSQYARARKDFMLSSHDSVYEIK HPL-Pepper
333 SLLKSVVYEALRIEPPVPFQYGKAKEDIVIQSHDSSFKIK HPL-Melon

    KGELLCGYQPFATKDPKVF-DRPEEFVPDRFVGE-GEELL Majority
             450       460       470       480
431 EGEMLFGYQPFATKDPKIF-DRPEEFVADRFVGE-GVKLM AOS-Flax
368 KGEMLFGYQPFATKDPKVF-DRPEEFVPDRFVGD-GEALL AOS-Guayule
411 AGEMLYGYQPLATRDPKIF-DRADEFVPERFVGEEGEKLL AOS-Arabi
426 EGEVICGYQPFATRDPKIF-DRADELVPDRFTGE-GEELL AOS-Melon
393 KGELLCGYQKVVMTDPKVFDE-PESFNSDRFVQNS--ELL HPL-Guava
382 KGELLCGYQPLVMRDPAVFDD-PETFAPERFM-GSGKELL HPL-Banana
383 KGELLCGYQPLVMKDPKVFDE-PEKFMLERFTKEKGKELL HPL-Pepper
373 KGETIFGYQPFATKDPKIFKD-SEKFVGDRFVGEEGEKLL HPL-Melon
```

FIG.1F

```
    K Y V F W S N G P E T G T P T V A N K Q C A G K D F V V L I A R L F V A E L F R  Majority
                      490                           500                           510                           520

469 E Y V M W S N G P E T E T P S V A N K Q C A G K D F V V M A A R L F V V E L F K  AOS-Flax
406 K Y V W W S N G P E T E S P T V E N K Q C A G K D F V V L I T R L F V I E L F R  AOS-Guayule
450 R H V L W S N G P E T E T P T V G N K Q C A G K D F V V L V A R L F V I E I F R  AOS-Arabi
464 K H V I W S N G P E T Q S P S V Q N K Q C A G K D F I V F I S R L L V V E L F L  AOS-Melon
430 D Y L Y W S N G P Q T G T P T E S N K Q C A A K D Y V T L T A C L F V A Y M F R  HPL-Guava
420 K Y V F W S N G P E T G T P T P A N K Q C A A K D Y V V E T A C L L M A E I F Y  HPL-Banana
422 N Y L F W S N G P Q T G S P T E S N K Q C A A K D A V T L T A S L I V A Y I F Q  HPL-Pepper
412 K Y V Y W S N E R E T V E P T A E N K Q C P G K N L V V L I G R I M V V E F F L  HPL-Melon

    R Y D S F D I E V G S S P L G A A V T - - - - - - - T S L K - - - - -            Majority
                      530                           540                           550

509 R Y D S F D I E V G T S S L G A S I T - - - - - - L T S L K R S T F              AOS-Flax SEQ ID NO:53
446 R Y D S F E I E L G E S P L G A A V T - - - - - - L T F L K R A S I              AOS-Guayule SEQ ID NO:54
490 R Y D S F D I E V G T S P L G S S V N - - - - - - F S S L R K A S F              AOS-Arabi SEQ ID NO:55
504 R Y D S F D I E A S N T P L G A A V T V S A A V T V T S L K K A S F              AOS-Melon SEQ ID NO:52
470 R Y N S V T G S S S S I T A V E K A N                                            HPL-Guava SEQ ID NO:38
460 R Y D E F V C A D D A I S V T K L D R A R E W E                                  HPL-Banana SEQ ID NO:33
462 K Y D S V S F S S G S L T S V K K A C                                            HPL-Pepper SEQ ID NO:32
452 R Y D T F T V E V A D L P L G P A V K F K S L T R A T D M V                      HPL-Melon SEQ ID NO:7
```

Decoration 'Decoration #1 : Shade (with solid black) residues that match the Consensus exactly

FIG.1G

Sequences of the degenerate primers

Primer 1:

Primer 1A

```
 G   E   L   L   C   G   Y  Q     SEQ ID NO:22
GGT GAG TTG CTN TGY GGN TAY CA    SEQ ID NO:16
(64-fold degenerate)
```

Primer 1B

```
 G   E   L   L   C   G  Y         SEQ ID NO:23
GGT GAG TTG CTN TGY GGN TA        SEQ ID NO:17
(32-fold degenerate)
```

Primer 2:

```
W   S   N   G   P   E   T         SEQ ID NO:24

Antisense of:-
TGG TCN AAY GGN CCR GAG AC        SEQ ID NO:18
(64-fold degenerate)
```

Primer 3:

```
 Y   W   S   N   G   P   E  T     SEQ ID NO:25
TAC-TGG-TCN-AAY-GGN-CCN SAR AC    SEQ ID NO:19
(32-fold degenerate)
```

Primer 4:

Primer 4A

```
N   K   Q   C   A   A   X   X     SEQ ID NO:26

Antisense of:-
AAY AAR CAR TGY GCN GCT AAG GAC   SEQ ID NO:20
(64-fold degenerate)
```

Primer 4B

```
     K   Q   C   A   A   X   X    SEQ ID NO:27

Antisense of:-
    AAR CAR TGY GCN GCT AAG GAC   SEQ ID NO:21
(32-fold degenerate)
```

FIG.3

AMINO ACID SEQUENCE ALIGNMENT OF THE 3 DIFFERENT "150 bp" CLONE

```
                  Primer 1
SEQ ID NO:28     ---------->
        Clone A  G E L L C G Y Q P L V M R D P K V F D E P E A F N P D R F R G E

SEQ ID NO:29
        Clone B  G E L L C G Y Q P F A T R D P K I F D R A D E F V P D R F T G E

SEQ ID NO:30
        Clone C  G E L L C G Y Q P F A T K D P K I F K D S E K F V G D R F V G E

                               Primer 2
                          <-----------
Clone A  K G V A L L D Y L F W S N G P Q T

Clone B  - G E E L L K H V I W S N G P E T

Clone C  E G E K L L K Y V Y W S N G P E T
```

■ Typical motif of AOS

■ Typical motif of HPL

■ Consensus AA

Clone A and clone B: 65% identity
Clone A and clone C: 57% identity
Clone B and clone C: 72% identity

FIG.4

% SIMILARITY BETWEEN THE C-TERMINAL PROTEIN SEQUENCES OF CLONES A, B, C (APPROX 100 AMINO ACIDS) COMPARED TO THE EQUIVALENT REGIONS OF PUBLISHED 13-HPL OR AOS SEQUENCES

| | 13-HPL | | | AOS | | |
|---|---|---|---|---|---|---|
| | GUAVA | PEPPER | BANANA | FLAX | GUAYULE | ARABID |
| CLONE A | 71 | 69 | 62 | 51 | 50 | 51 |
| CLONE B | 35 | 41 | 43 | 64 | 68 | 66 |
| CLONE C | 32 | 34 | 36 | 51 | 56 | 53 |

MUSKMELON (*CUCUMIS MELO*) HYDROPEROXIDE LYASE AND USES THEREOF

This is a continuation of application Ser. No. 09/537,357, filed Mar. 29, 2000, now U.S. Pat. No. 6,271,018.

BACKGROUND OF THE INVENTION

1. Field of the Invention

The present invention relates to a fatty acid hydroperoxide lyase protein, which has activity for 9-hydroperoxide substrates and which is present in muskmelon (*Cucumis melo*), and the gene encoding the protein. The present invention also relates to the means for expressing the hydroperoxide lyase and methods of using the lyase in the field of organic synthesis.

2. Background Art

Plants produce various volatile compounds that give rise to the characteristic flavors and odors of the particular plant. Unsaturated fatty acids like linoleic and linolenic acids are precursors of flavor compounds such as n-hexanal, hexan-1-ol, 2(E)-hexen-1-al, 2(E)-hexen-1-ol, 3(Z)-hexen-1-al, 3(Z)-hexen-1-ol (also known as pipol), 3-(Z)-nonenal, (3Z,6Z)-nonadienal, 3-(Z)-nonenol, (3Z,6Z)-nonadienol, 2-(E)-nonenal, (2E,6Z)-nonadienal, 2-(E)-nonenol, and (2E,6Z)-nonadienol. These compounds are used widely in flavors, particularly fruit flavors, and are used by the aroma industry for a fruit aroma. The demand for these flavor compounds has grown to exceed their supply from traditional sources, thus motivating research efforts toward finding alternative natural ways of obtaining these materials.

The synthesis of these flavor compounds starts from free (polyunsaturated) fatty acids such as linoleic (9(Z), 12(Z)-octadecadienoic) and α-linolenic (9(Z), 12(Z), 15(Z)-octadecatrienoic) acids. In nature, these acids are released from cell membranes by lipolytic enzymes after cell damage. Fatty acid hydroperoxides are formed by the action of a lipoxygenase (LOX) and are subsequently cleaved by a hydroperoxide lyase to give $C_6$- and $C_9$-volatile flavor compounds together with ω-oxoacids. The cleavage of 13-hydroperoxides yields $C_6$-compounds, including hexanal and (3Z)-hexenal, and the cleavage of 9-hydroperoxides yields $C_9$-compounds, (3Z)-nonenal and (3Z,6Z)-nonadienal. In the presence of isomerases, these aldehydes are isomerized to (2E)-enals. Furthermore, alcohol dehydrogenases can convert the aldehydes into their corresponding alcohols.

The HPL enzymes have proven difficult to study because they are membrane bound and are present in only small quantities in plant tissue. The HPL enzymes have been characterized as 13-HPLs or 9-HPLs, according to their substrate specificity. The 13-HPL enzyme was identified for the first time in banana fruits (Tressl and Drawert, 1973) and was subsequently studied in a number of different plant materials, including watermelon seedlings (Vick and Zimmerman, 1976), apple and tomato fruits (Schreier and Lorenz, 1982), tomato leaves (Fauconnier et al., 1997), cucumber seedlings (Matsui, et al, 1989), and soybean seedlings (Olias et al., 1990). The 13-HPL enzyme has been purified from tea leaves (Matsui et al., 1991) and, more recently, from green bell pepper fruits (Shibata et al., 1995), tomato leaves (Fauconnier et al., 1997), sunflower (Itoh and Vick, 1999), guava (PCT application, WO 9958648 A2), and banana (European Patent Application, Publication No. EP 0801133 A2). A 9-hydroperoxide specific HPL has been identified in pear (Kim and Grosch, 1981). There have been studies that suggested the presence of a third type of HPL that cleaves both 9- and 13-hydroperoxides. (Natsui et al. 1989; Homostaj and Robinson, 1998).

Crude sources of lyases are currently used in an industrial process for the production of flavors and aromas. (See, e.g., U.S. Pat. No. 5,464,761). In this process, a solution of the required substrates made from linoleic or linolenic acid (obtained from sunflower and linseed oils, respectively) using freshly prepared soybean flour as a source of LOX. This solution is then mixed with a freshly prepared puree of whole fruit, as the crude source of HPL. The aldehyde products are then isolated by distillation. When the alcohols are required, fresh baker's yeast is added to the hydroperoxide solution before it is mixed with the fruit puree. This yeast contains an active alcohol dehydrogenase enzyme that reduces the aldehydes as they are formed by the HPL.

There are a number of disadvantages to this industrial process. The principal disadvantage is the requirement of large quantities of fresh fruit. Such a requirement means that the process has to be operated in a country where fresh fruit is cheaply and freely available. Even when such a site is found, availability is limited to the growing season of the fruit.

A second disadvantage is that the desired enzyme activities are rather dilute in the sources employed. This means that relatively large amounts of soy flour, fruit puree, and yeast have to be used in the process. The large volumes of these crude materials that are required for industrial production place physical constraints on the yields of flavor and aroma compounds that can be achieved.

A third disadvantage is that it is a large-volume batch process, which, by its nature, does not make maximum use of the HPL's catalytic activity, is relatively labor intensive, and generates a large amount of residual organic material. The residual organic material must subsequently be transported to a compost farm or otherwise discarded.

The present invention overcomes these limitations and disadvantages related to the source of muskmelon 9-HPL by providing purified and recombinant muskmelon 9-HPL proteins, nucleic acids, expression systems, and methods of use thereof.

SUMMARY OF THE INVENTION

The present invention provides a fatty acid lyase and a nucleic acid encoding the lyase. In particular, an isolated fatty acid hydroperoxide lyase is disclosed, wherein the activity of the lyase for 9-hydroperoxide substrates is greater than the activity for 13-hydroperoxide substrates and wherein $K_m$ and $V_{max}$ of the lyase for 9-hydroperoxylinolenic acid are greater than $K_m$ and $V_{max}$ of the lyase for 9-hydroperoxylinoleic acid. More particularly, the invention provides a lyase present in melon (*Cucumis melo*), and a nucleic acid encoding the lyase. The invention also provides a vector, comprising the nucleic acid of the invention, and expression systems with which the recombinant lyase can be obtained.

The invention also provides methods of using the lyase of the invention, including a method of cleaving a (9S, 10E, 12Z) 9-hydroperoxyoctadeca-10,12-dienoic acid or (9S, 10E, 12Z, 15Z) 9-hydroperoxyoctadeca-10,12,15-trienoic acid into a C9-aldehyde and a C9-oxononanoic acid and a method of cleaving (9Z, 11E, 13S) 13-hydroperoxyoctadeca-9,11-dienoic acid or (9Z, 11E, 13S, 15Z) 13-hydroperoxyoctadeca-9,11,15-trienoic acid into a C6-aldehyde and a C12-oxocarboxylic acid. Also, the invention provides a method of preparing 3-(Z)-nonenal, (3Z,6Z)-nonadienal, 2-(E)-nonenal, (2E,6Z)-nonadienal, or their corresponding alcohols from (9S, 10E, 12Z) 9-hydroperoxyoctadeca-10,12-dienoic acid or (9S, 10E, 12Z, 15Z)9-hydroperoxyoctadeca-10,12,15-trienoic acid using the lyase of the present invention. Also provided is a method of preparing n-hexanal, 3-(Z)-hexen-1-al, 2-(E)-hexen-1-al, or their corresponding alcohols from (9Z, 11E, 13S) 13-hydroperoxyoctadeca-9,11-dienoic acid or (9Z, 11E, 13S, 15Z) 13-hydroperoxyoctadeca-9,11,15-trienoic acid using the lyase of the present invention.

BRIEF DESCRIPTION OF THE DRAWINGS

FIG. 3 shows the sequences of the degenerate primers used to obtain the 150 bp and 70 bp fragments of melon HPL and AOS.

FIG. 4 shows the amino acid sequence alignment of three different 150 bp clones of melon HPL and AOS. Clone A and B have 65% identity, whereas clone A and C have 57% and B and C have 72% identity in amino acid sequences.

DETAILED DESCRIPTION OF THE INVENTION

Figure 1A:
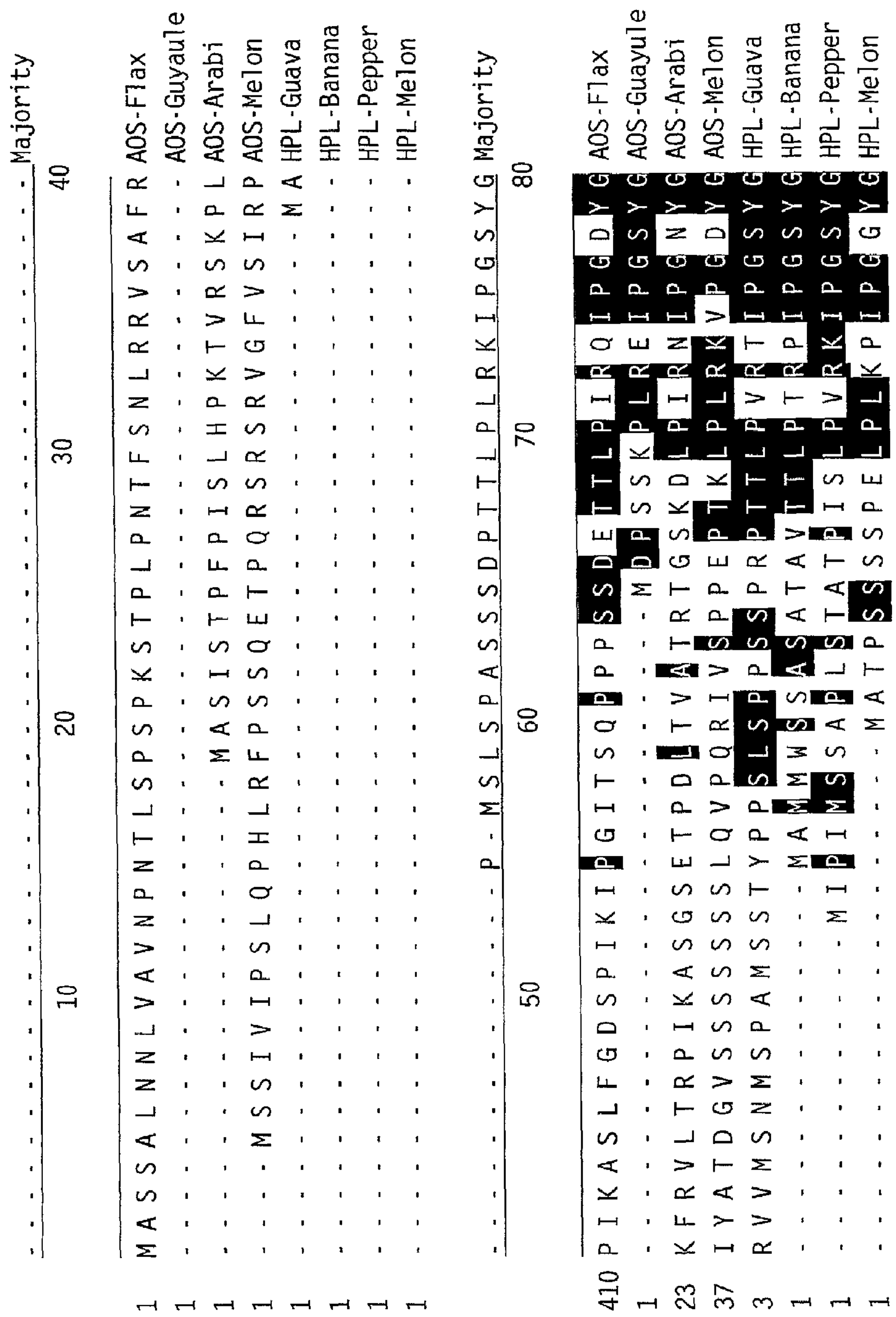
FIG. 1 shows the full length amino acid sequences for Guava-HPL, Banana-HPL, Pepper-HPL, Arab-AOS, Flax-AOS, Guayule-AOS, Melon AOS, and the Melon 9-HPL with the regions having a high degree of identity shown in dark boxes and the consensus sequence labeled as "majority."

The present invention may be understood more readily by reference to the following detailed description of preferred embodiments of the invention and the Examples included therein.

Before the present methods are disclosed and described, it is to be understood that this invention is not limited to specific methods or to particular formulations, as such may, of course, vary. It is also to be understood that the terminology used herein is for the purpose of describing particular embodiments only and is not intended to be limiting.

As used in the specification and in the claims, "a" can mean one or more, depending upon the context in which it is used.

A. Proteins and Nucleic Acids

The present invention provides a fatty acid lyase and a nucleic acid encoding the lyase. In particular, an isolated fatty acid hydroperoxide lyase is disclosed, wherein the activity of the lyase for 9-hydroperoxide substrates is greater than the activity for 13-hydroperoxide substrates and wherein $K_m$ and $V_{max}$ of the lyase for 9-hydroperoxylinolenic acid are greater than $K_m$ and $V_{max}$ of the lyase for 9-hydroperoxylinoleic acid. More particularly, the invention provides a lyase present in melon (*Cucumis melo*), but not in cucumber (*Cucumis sativus*), and a nucleic acid encoding such polypeptide or protein. Thus, the lyase has an amino acid sequence present in a protein isolated from *Cucumis melo*, but does not have an amino acid sequence in a protein isolated from cucumber (*Cucumis sativus*).

The term "protein" refers to a polymer of amino acids and can include full-length proteins and polypeptides and fragments thereof. In the present invention, "lyase" means a protein having at least one lyase function. In particular, the term "9-hydroperoxide lyase," "9-HPL," and "functional 9-hydroperoxide lyase" mean a lyase protein having at least one function exhibited by a native 9-hydroperoxide lyase. For example, 9-HPL function can include the catalytic activity of cleaving a fatty acid 9-hydroperoxide into a C-9 aldehyde and a C-9-oxononanoic acid. Additionally, the disclosed lyases can have the following characteristics of native 9-HPL: antigenic determinants, binding regions, or the like.

The disclosed 9-HPL prefers 9-hydroperoxide substrates rather than 13-hydroperoxide substrates but has both 9-HPL and 13-HPL functions. The terms "13-hydroperoxide lyase," "13-HPL," and "functional 13-hydroperoxide lyase" refer to a lyase protein having at least one function exhibited by a native 13-hydroperoxide lyase. For example, 13-HPL function can include the catalytic activity of cleaving a fatty acid 9-hydroperoxide into a C-6 aldehyde and a C-12-ω-oxoacid moiety. Additionally, the disclosed lyases can have the following characteristics of native 13-HPL: antigenic determinants, binding regions, or the like.

The lyase of the present invention can comprise additional amino acids, such as amino acids linked to the N-terminal end or amino acids linked to the C-terminal end or amino acids inserted within the lyase sequence, as long as the resulting protein or peptide retains a lyase function, such as the preferred lyase function. Furthermore, the lyase can contain various mutations in the amino acid sequence compared to the amino acid sequence of a native lyase, so long as at least one lyase function is maintained. More specifically, the disclosed lyase cleaves 9-hydroperoxylinoleic substrates (e.g., (9S, 10E, 12Z) 9-hydroperoxyoctadeca-10, 12-dienoic acid), 9-hydroperoxylinolenic substrates (e.g., (9S, 10E, 12Z, 15Z) 9-hydroperoxyoctadeca-10,12,15-trienoic acid), 13-hydroperoxylinoleic substrates (e.g., (9Z, 11E,13S)13-hydroperoxyoctadeca-9,11-dienoic acid), and 13-hydroperoxylinolenic substrates (e.g., (9Z, 11E, 13S, 15Z) 13-hydroperoxyoctadeca-9,11,15-trienoic acid). The $K_m$ and $V_{max}$ of the lyase for 9-hydroperoxylinolenic acid are greater than $K_m$ and $V_{max}$ of the lyase for 9-hydroperoxylinoleic acid.

The lyase has a characteristic affinity for various substrates. The lyase has a greater affinity for 13-hydroperoxide substrates, and the $K_m$ of the lyase for 9-hydroperoxide substrates is greater than for 13-hydroperoxide substrates. The computed $K_m$ is as follows: 9-hydroperoxylinolenic acid >9-hydroperoxylinoleic acid>13-hydroperoxylinoleic acid. The $K_m$ of the lyase for 13-hydroperoxylinoleic acid is approximately the same as the affinity for 13-hydroperoxylinolenic acid. More specifically, the computed $K_m$ for 9-hydroperoxylinoleic acid is approximately 192 μM with 95% confidence limits as 142–242 and is approximately 45–60%, and preferably approximately 54%, of the $K_m$ of the lyase for 9-hydroperoxylinolenic acid. The computed $K_m$ for 13-hydroperoxylinolenic acid is approximately 50 μM with 95% confidence limits as 41–59 and is approximately 15–35%, and preferably approximately 26%, of the $K_m$ of the lyase for 9-hydroperoxylinolenic acid. The computed $K_m$ for 13-hydroperoxylinolenic acid is approximately 51 μM with 95% confidence limits as 37–65 and is approximately 15–35%, and preferably approximately 27%, of the $K_m$ of the lyase for 9-hydroperoxylinolenic acid.

The disclosed lyase cleaves each type of substrate with a characteristic rate. The lyase reacts faster with the 9-hydroperoxide substrates, and the $V_{max}$ of the lyase for 9-hydroperoxide substrates is greater than the $V_{max}$ for 13-hydroperoxide substrates. The rate of cleavage of the various substrates by the lyase of the invention, as indicated by $V_{max}$, is as follows:9-hydroperoxylinolenic acid>9-hydroperoxylinoleic acid >13-hydroperoxylinoleic acid. The rate for 13-hydroperoxylinoleic acid is approximately the same as the rate for 13-hydroperoxylinolenic acid. More specifically, $V_{max}$ of the lyase for 9-hydroperoxylinoleic acid is approximately 45–60%, and preferably approximately 55%, of the $V_{max}$ of the lyase for 9-hydroperoxylinolenic acid. $V_{max}$ of the lyase for 13-hydroperoxylinoleic acid is approximately 25–35%, and preferably approximately 30%, of the $V_{max}$ of the lyase for 9-hydroperoxylinolenic acid. $V_{max}$ of the lyase for 13-hydroperoxylinolenic acid is approximately 20–30%, and preferably approximately 22%, of the $V_{max}$ of the lyase for 9-hydroperoxylinolenic acid. By "approximately the same" rate or affinity is meant that the rate or affinity for one substrate, e.g., 13-hydroperoxylinolenic acid, as expressed as a percentage of the rate or affinity for 9-hydroperoxylinolenic acid, is within 10%, and preferably within 5%, of a second substrate, e.g., 13-hydroperoxylinoleic acid, also expressed as a percentage of the rate or affinity for 9-hydroperoxylinolenic acid.

The disclosed lyase has a molecular weight of about 45–65 kDa, preferably about 50–60 kDa, and even more preferably about 55 kDa. The optimal pH for the disclosed lyase is greater than 6, preferably about 6.5–8.5, more preferably 7.0–8.0, and even more preferably 7.2–7.6. The enzyme has approximately 25% of maximal activity at pH 5.0 and approximately 15% of maximal activity at pH 9.0.

The disclosed lyase is isolated. Isolation of the lyase can occur in a variety of ways. For example, the lyases can be purified, or partially purified, from a source, such as *Cucumis melo*, using standard biochemical techniques. See, for example, Hornostaj and Robinson (1998). Alternatively, the lyase can be synthesized using protein synthesis techniques known in the art or can be recombinantly produced, through recombinant DNA technology and the use of genetically engineered expression systems. Synthesized or recombinantly produced lyase can be tagged with histidines to promote isolation. Thus, a preferred isolation method for recombinantly produced lyase is the use of nickel columns, which bind histidine residues. Histidine residues can be added to the amino terminal end of the disclosed lyase to act as a tag for the protein. The use of histidine tags or other tags is well know to one of ordinary skill in the art.

In one embodiment, the disclosed lyase comprises amino acids unique to *Cucumis melo*, as set forth in FIG. 1, that provide the activity of cleaving 9-hydroperoxide substrates with greater activity than 13-hydroperoxide substrates and that provide the activity of cleaving 9-hydropoxylinoleic acid with less than 1.6 times the activity as 9-hydroperoxylinolenic acid.

The invention also provides an isolated protein, comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, and SEQ ID NO:15. The amino acid sequence of SEQ ID NO:15 has been submitted to the GenBank database under accession number AF081955.

The invention provides an isolated nucleic acid that encodes the disclosed lyase. The cDNA of the 9-HPL from *Cucumis melo* has been cloned and sequenced (SEQ ID NO:8). The amino acid sequence of the protein encoded by the *Cucumis melo* cDNA is also disclosed (SEQ ID NO:7). In one embodiment, the nucleic acid comprises the nucleic acid sequence set forth in SEQ ID NO:8. In another embodiment, the nucleic acid comprises the nucleic acid sequence set forth in SEQ ID NO:56. The nucleic acid sequence of SEQ ID NO:56 has been submitted to the GenBank database under accession number AF081955.

Further provided are isolated nucleic acids that encode the protein having an amino acid sequence selected from the group consisting of SEQ ID NO:1, SEQ ID NO:2, SEQ ID NO:3, SEQ ID NO:4, SEQ ID NO:5, SEQ ID NO:6, and SEQ ID NO:7. Recombinant systems include expression systems in both prokaryotic and eukaryotic cells and include expression of the lyase having the native protein sequence or the lyase having a protein sequence altered from the native sequence in some way. The melon 9-HPL cDNA was cloned and sequenced and the nucleotide sequence for the full-length cDNA was determined to be 1446 base pairs (SEQ ID NO:8), which includes a stop codon. The translated sequence encodes a total of 481 amino acids residues (SEQ ID NO:7), corresponding to a protein with a calculated molecular weight of about 55,000 Daltons.

As shown in FIG. 1, the derived full length amino acid sequence shows a degree of homology (identity and similarity) to a number of HPLs and allene oxide synthases (AOS). For example, there is a degree of homology between the disclosed amino acid sequence and the 13-HPLs of guava, banana, and pepper. There is also homology between the disclosed HPL and AOS-Flax, AOS-Guayule, AOS Arabi, and AOS-Melon. However, FIG. 1 clearly demonstrates that there are regions for the disclosed lyase that are unique relative to other HPLs and AOSs. Particularly these regions are unique to 9-HPLs and furthermore these regions are unique to *Cucumis melo*.

Taking into account deletions and insertions, the alignment in FIG. 1 and Table 1 reveal that, using the Clustal method with PAM250 residue weight chart available through the MegAlign subprogram of Lasergene (Dnastar, Madison, Wis.), the melon 9-HPL amino acid sequence has about a 45.7% similarity with AOS-Flax, about a 46% similarity with AOS-Guayule, about a 48.0% similarity with AOS-Arabi, about a 47% similarity with AOS-Melon, about a 60% similarity with HPL-Guava, about a 58% similarity with HPL-Banana, and about a 60% similarity with HPL-Pepper.

"Similarity" can include amino acid residues that are either the same or similar. Similar amino acids are indicated in Table 2. Despite these similarities, there are uniques regions of the disclosed lyase. Preferred unique regions are set forth in SEQ ID NO: 1 (MATPSSSSPE), SEQ ID NO: 2 (ILFDTAKVEKRNILD), SEQ ID NO:3 (RLFLSFLA), SEQ ID NO:4 (SISDSMS), SEQ ID NO:5 (LLSDGTPD), and SEQ ID NO:6 (IFSVFEDLVI). Proteins that contain these regions and function as the disclosed lyase are provided. Particularly preferred embodiments are those that have at least one of these defined regions set forth in SEQ ID NOs:1–6 that retain 9-HPL function. More preferred embodiments are those that have at least two of these defined regions set forth in SEQ ID NOs:1–6 present and that retain 9-HPL function. More preferred embodiments are those that have at least three of these defined regions set forth in SEQ ID NOs:1–6 and that retain 9-HPL function. More preferred embodiments are those that have at least four of these defined regions set forth in SEQ ID NOs:1–6 and that retain 9-HPL function. Even more preferred embodiments are those that have at least five of these defined regions set forth in SEQ ID NOs:1–6 and that retain 9-HPL function. Most preferred embodiments are those that have at least six of the regions set forth in SEQ ID NOs:1–6 and that retain 9-HPL function.

| | Percent Similarity | | | | | | | | |
|---|---|---|---|---|---|---|---|---|---|
| Percent Divergence | 1 | 2 | 3 | 4 | 5 | 6 | 7 | 8 | |
| 1 | | 59.2 | 56.5 | 59.4 | 36.2 | 37.2 | 34.9 | 44.7 | 1 AOS-Flax |
| 2 | 33.6 | | 57.0 | 55.8 | 42.1 | 46.1 | 43.8 | 55.5 | 2 AOS-Guayule |
| 3 | 40.6 | 39.5 | | 56.8 | 37.8 | 38.9 | 36.7 | 47.8 | 3 AOS-Arabi |
| 4 | 38.3 | 36.6 | 40.4 | | 35.1 | 37.6 | 33.0 | 45.8 | 4 AOS-Melon |
| 5 | 58.9 | 56.6 | 60.7 | 60.9 | | 60.5 | 67.3 | 42.3 | 5 HPL-Guava |
| 6 | 56 1 | 55.4 | 57.2 | 56.2 | 39.6 | | 58.4 | 46.4 | 6 HPL-Banana |
| 7 | 59.2 | 58.7 | 60.4 | 61.5 | 32.4 | 45.0 | | 44.3 | 7 HPL-Pepper |
| 8 | 47.1 | 46.4 | 47.5 | 47.2 | 59.6 | 57.5 | 59.3 | | 8 HPL-Melon |
| | 1 | 2 | 3 | 4 | 5 | 6 | 7 | 8 | |

It is understood that the disclosed lyase includes functional variants. These variants are produced by making amino acid substitutions, deletions, and insertions, as well as post-translational modifications. Such variations may arise naturally as allelic variations (e.g., due to genetic polymorphism) or may be produced by human intervention (e.g., by mutagenesis of cloned DNA sequences), such as induced point, deletion, insertion and substitution mutants. These modifications can result in changes in the amino acid sequence, provide silent mutations, modify a restriction site, or provide other specific mutations.

Amino acid sequence modifications fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues but may include multiple substitutions at different positions; insertions usually will be on the order of about from 1 to 10 amino acid residues but can be more; and deletions will range about from 1 to 30 residues, but can be more. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with Table 2 and are referred to as conservative substitutions.

TABLE 2

Amino Acid Substitutions

| Original Residue | Exemplary Substitutions |
|---|---|
| Ala | ser |
| Arg | lys |
| Asn | gln |
| Asp | glu |
| Cys | ser |
| Gln | asn |
| Glu | asp |
| Ala | ser |
| Gly | pro |
| His | gln |
| Ile | leu; val |
| Leu | ile; val |
| Lys | arg; gln |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (Creighton,1983), acetylation of the N-terminal amine and, in some instances, amidation of the C-terminal carboxyl.

In all mutational events, it is understood that the controlling aspect of the mutation is the function that the subsequent protein possesses. The most preferred mutations are those that do not detectably change the 9-HPL function. For example as described above the disclosed lyase has very specific kinetic characteristics and preferred mutations would be those that for example produce mutated 9-HPLs that preferentially cleave 9-hydroperoxide substrates.

There are numerous assays for determining the relative function of the disclosed lyases, including, for example, HPLC analysis, spectrophotometric analysis, gas chromatographic analysis, and gas chromatography with mass spectrometric analysis.

It is also understood that mutational events may at times include mutations that alter the activity in a defined way, for example, by increasing the $V_{max}$ of cleavage of 9-hydroperoxide substrates. Should these types of mutations be desired, close analysis of the reaction rates and function of the mutated proteins will allow isolation of mutant lyases that either function better or worse than native lyases. Preferred mutations are those that increase the activity of the lyase for cleavage of 9-hydroperoxide substrates.

It is also understood that there is degeneracy in the relationship between nucleic acids and proteins so that there can be multiple nucleic acid codons for a given protein sequence. Thus, the melon cDNA, while not having the same sequence as the DNA isolated from *Cucumis melo*, encodes the same amino acid sequence of the lyase isolated from *Cucumis melo*. In addition, there are numerous reasons one may wish to alter the sequence of the *Cucumis melo* cDNA while maintaining the unique coding of the *Cucumis melo* protein. For example, one may wish to insert or remove specific nucleic acid restriction enzyme sites contained or desired in the cDNA.

Particularly preferred embodiments incorporate both the functional variants incorporating non-conserved amino acids described above in combination with the unique regions set forth in SEQ ID NOs:1–6. Most preferred is the functional 9-HPL isolated from *Cucumis melo* having the sequence set forth in SEQ ID NO:7.

Also disclosed are nucleic acid sequences that encode the proteins disclosed herein. These nucleic acids would include those that encode a protein possessing at least one of the unique amino acid sequences disclosed in SEQ ID NOs:1–6. This would include as discussed above all degenerate sequences to the nucleic acids encoding these proteins. One embodiment is the nucleic acid representing the cDNA isolated from *Cucumis melo*, as set forth in SEQ ID NO:8.

Also disclosed are isolated nucleic acids, which specifically hybridize with the nucleic acid of SEQ ID NO:8 under stringent conditions of hybridization. Preferably the nucleic acids that hybridize with the nucleic acid of SEQ ID NO:8 under stringent conditions do not hybridize at the stringent conditions with a nucleic acid encoding a lyase present in *Cucumis sativus*. Most preferably the isolated nucleic acid encodes a protein that has a 9-HPL function.

"Stringent conditions" refers to the washing conditions used in a hybridization protocol or in a primer/template hybridization in a PCR reaction. In general, these conditions should be a combination of temperatures and salt concentrations for washing chosen so that the denaturation temperature is approximately 5–20° C. below the calculated $T_m$ (melting/denaturation temperature) of the hybrid under study. The temperature and salt conditions are readily determined empirically in preliminary experiments in which samples of reference nucleic acid are hybridized to the primer nucleic acid of interest and then amplified under conditions of different stringencies. The stringency conditions are readily tested and the parameters altered are readily apparent to one skilled in the art. For example, $MgCl_2$ concentrations used in PCR buffer can be altered to increase the specificity with which the primer binds to the template, but the concentration range of this compound used in hybridization reactions is narrow, and, therefore, the proper stringency level is easily determined. For example, hybridizations with oligonucleotide probes 18 nucleotides in length can be done at 5–10° C. below the estimated $T_m$ in 6×SSPE, then washed at the same temperature in 2×SSPE. The $T_m$ of such an oligonucleotide can be estimated by allowing 2° C. for each A or T nucleotide, and 4° C. for each G or C. An 18 nucleotide probe of 50% G+C would, therefore, have an approximate $T_m$ of 54° C. Likewise, the starting salt concentration of an 18 nucleotide primer or probe would be about 100–200 mM. Thus, stringent conditions for such an 18 nucleotide primer or probe would be a $T_m$ of about 54° C. and a starting salt concentration of about 150 mM and modified accordingly by preliminary experiments. $T_m$ values can also be calculated for a variety of conditions utilizing commercially available computer software (e.g., OLIGO®).

The present invention further provides an isolated nucleic acid which specifically hybridizes with the nucleic acid encoding the amino acid sequence of melon 9-HPL, as set forth in SEQ ID NO:7, under stringent conditions of hybridization. Preferably, the isolated nucleic acid does not hybridize at the stringent conditions to a nucleic acid set encoding a lyase present in *Cucumis sativus*. Most preferably the isolated nucleic acid encodes a protein that has a 9-HPL function.

Preferably, the isolated nucleic acid of the invention has at least 99, 98, 97, 95, 90, 85, 80, 75, or 70% complementarity with the sequence to which it hybridizes. More preferred embodiments are isolated nucleic acids that have at least 90% complementarity with the sequence to which it hybridizes. More preferred embodiments are isolated nucleic acids that have at least 80% complementarity with the sequence to which it hybridizes. More preferred embodiments are isolated nucleic acids that have at least 70% complementarity with the sequence to which it hybridizes. The percent complementarity can be based preferably on a nucleotide-by-nucleotide comparison of the two strands. Specific methods of determining complementarity are well known in the art (e.g., the Clustal, Jotun Hein, WilburLipman, Martinez Needleman-Wunsch, Lipman-Pearson, and Dotplot methods). A skilled artisan, therefore, would understand the meaning of the term and would know how to determine complementarity between two sequences.

The nucleic acid can also be a probe or a primer, for example, to detect or amplify target nucleic acids. Typically, a unique nucleic acid useful as a primer or probe will be at least about 20 to about 25 nucleotides in length, depending upon the specific nucleotide content of the sequence. Additionally, fragments can be, for example, at least about 30, 40, 50, 75, 100, 200, 400, or any number in between in nucleotide length. Alternatively, a full length sequence or a sequence that is longer than a full length sequence can be used.

B. Vectors

The invention provides a vector, comprising the nucleic acid of the invention. The present invention also provides vectors comprising a nucleic acid that encodes a 9-hydroperoxide lyase, including, for example, a lyase having an amino acid sequence present in a protein isolated from *Cucumis melo*. More specifically, the vector can be a plasmid. Even more specifically, the vector can comprise a promoter functionally linked to one of the nucleic acids of the present invention.

"Vector" means any carrier containing exogenous DNA. Thus, vectors are agents that transport the exogenous nucleic acid into a cell without degradation and include a promoter yielding expression of the nucleic acid in the cells into which it is delivered. "Vectors" include but are not limited to plasmids, viral nucleic acids, viruses, phage nucleic acids, phages, cosmids, and artificial chromosomes. A variety of prokaryotic and eukaryotic expression vectors suitable for expression of the functional lyase of the invention can be produced. Such expression vectors include, for example, pET, pET3d, pCR2.1, pBAD, pUC, and yeast vectors. The vectors can express the described lyase, for example, in a variety of in vivo and in vitro situations.

Viral vectors include adenovirus, adeno-associated virus, herpes virus, vaccinia virus, polio virus, AIDS virus, neuronal trophic virus, Sindbis and other RNA viruses, including these viruses with the HIV backbone. Also preferred are any viral families which share the properties of these viruses which make them suitable for use as vectors. Retroviral vectors, which are described in Verma (1985), include Murine Maloney Leukemia virus, MMLV, and retroviruses that express the desirable properties of MMLV as a vector. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA.

A "promoter" is generally a sequence or sequences of DNA that function when in a relatively fixed location in regard to the transcription start site. A "promoter" contains core elements required for basic interaction of RNA polymerase and transcription factors and may contain upstream elements and response elements.

"Enhancer" generally refers to a sequence of DNA that functions at no fixed distance from the transcription start site and can be either 5' (Laimins, 1981) or 3' (Lusky et al., 1983) to the transcription unit. Furthermore, enhancers can be within an intron (Baneiji et al., 1983) as well as within the coding sequence itself (Osborne et al., 1984). They are usually between 10 and 300 bp in length, and they function in cis. Enhancers function to increase transcription from nearby promoters. Enhancers, like promoters, also often contain response elements that mediate the regulation of transcription. Enhancers often determine the regulation of expression. It is preferred that the promoter and/or enhancer region act as a constitutive promoter and/or enhancer to maximize expression of the region of the transcription unit to be transcribed.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs.

The vector can include nucleic acid sequence encoding a marker product. This marker product is used to determine if the gene has been delivered to the cell and once delivered is being expressed. Preferred marker genes are the *E. Coli* lacZ gene which encodes β-galactosidase and green fluorescent protein.

In some embodiments the marker may be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern and Berg, 1982), mycophenolic acid, (Mulligan and Berg, 1980) or hygromycin (Sugden et al., 1985).

Also disclosed are cells that containing an exogenous nucleic acid comprising the nucleic acid encoding the lyase or protein of the present invention. A preferred cell is a prokaryotic cell. Particularly preferred prokaryotic cells are *Escherichia coli* cell, a *Bacillus* cell, and a *Streptomyces* cell. These bacteria have the ability to secrete recombinant proteins, thus, avoiding the need for lysing the cells to isolate the protein.

Another preferred cell type containing an exogenous nucleic acid comprising the nucleic acid encoding the lyase or protein of the present invention is a eukaryotic cell. Particularly preferred eukaryotic cells are a yeast cell, a plant cell, and an insect cell. For example, *Pichia pastoris* or *Saccharomyces cerevisiae* can be used as an expression system. Appropriate means for transfection of the cells with the exogensous nucleic acid, including viral vectors, chemical transfectants, or physico-mechanical methods such as electroporation and direct diffusion of DNA, are well known in the art. See, for example, Wolff et al. (1990) and Wolff (1991), which are incorporated herein in their entirety by reference. The transfected cells can be used as a method of expressing the proteins and lyases of the present invention.

Many different strategies can be used to optimize expression of the protein or lyase of the present invention. Different enhancers are selected based on the host cell type, vector, and promoter. For example, isopropyl β-D-thiogalactopyranoside (IPTG) can be used as an inducer of the $P_{lac}$ promoter and derivatives of the $P_{lac}$ promoter when *E. coli* is the host cell. Inducer concentrations of IPTG range between 0–1 mM. Alternatively, a pBAD vector with a promoter that is induced by L-arabinose can be used in *E. coli*. Host cell type, vector, promoter, induction times, media compositions, temperature, cofactors, cultivation conditions, and cultivation times can be altered to optimize expression. Furthermore, the addition of a precursor of prosthetic groups like heme (including, for example, δ-aminolevulinic acid) can be used to optimize expression.

C. Methods of Using the Compositions

Disclosed is a method of cleaving a (9S, 10E, 12Z) 9-hydroperoxyoctadeca-10,12-dienoic acid or (9S, 10E, 12Z, 15Z) 9-hydroperoxyoctadeca-10,12,15-trienoic acid into a C9-aldehyde and a C9-oxononanoic acid, comprising the steps of contacting the disclosed lyase with the (9S, 10E, 12Z) 9-hydroperoxyoctadeca-10,12-dienoic acid or (9S, 10E, 12Z, 15Z)9-hydroperoxyoctadeca-10,12,15-trienoic acid. When (9S, 10E, 12Z) 9-hydroperoxyoctadeca-10,12-dienoic acid is the substrate, the C9-aldehyde is 3Z-nonenal. When (9S, 10E, 12Z, 15Z) 9-hydroperoxyoctadeca-10,12,15-trienoic acid is the substrate, the C9-aldehyde is 3Z, 6Z-nonadienal.

Also disclosed are methods of cleaving (9Z, 11E, 13S) 13-hydroperoxyoctadeca-9,11-dienoic acid or (9Z, 11E, 13S, 15Z) 13-hydroperoxyoctadeca-9,11,15-trienoic acid into a C6-aldehyde and a C12-oxocarboxylic acid, comprising contacting the disclosed lyase with the 13-hydroperoxyoctadeca-9,11-dienoic acid or 13-hydroperoxyoctadeca-9,11,15-trienoic acid.

Also disclosed are methods of preparing 3-(Z)-nonenal, (3Z,6Z)-nonadienal, 2-(E)-nonenal, (2E,6Z)-nonadienal, or their corresponding alcohols from (9S, 10E, 12Z) 9-hydroperoxyoctadeca-10,12-dienoic acid or (9S, 10E, 12Z, 15Z) 9-hydroperoxyoctadeca-10,12,15-trienoic acid, comprising the steps of contacting the (9S, 10E, 12Z) 9-hydroperoxyoctadeca-10,12-dienoic acid or (9S, 10E, 12Z, 15Z)9-hydroperoxyoctadeca-10,12,15-trienoic acid with the disclosed 9-HPL, thereby converting the (9S, 10E, 12Z) 9-hydroperoxyoctadeca-10,12-dienoic acid into 3-(Z)-nonenal or the (9S, 10E, 12Z, 15Z)9-hydroperoxyoctadeca-10,12,15-trienoic acid into (3Z,6Z)-nonadienal; and recovering the 3-(Z)-nonenal or (3Z,6Z)-nonadienal; reducing the 3-(Z)-nonenal into 3-(Z)-nonenol or the (3Z,6Z)-nonadienal into (3Z,6Z)-nonadienol and recovering the 3-(Z)-nonenol or (3Z,6Z)-nonadienol; or isomerizing the 3-(Z)-nonenal or (3Z,6Z)-nonadienal under temperature and pH conditions effective to obtain 2-(E)-nonenal or (2E,6Z)-nonadienal and either recovering the formed 2-(E)-nonenal or (2E,6Z)-nonadienal or reducing the 2-(E)-nonenal to 2-(E)-nonenol or the (2E,6Z)-nonadienal to (2E,6Z)-nonadienol and recovering the 2-(E)-nonenol or (2E,6Z)-nonadienol from the medium. The reducing step is preferentially carried out using an enzyme catalyzed reduction (e.g., using alcohol dehydrogenase) mediated by yeast using techniques known in the art. See, for example, EP 0 597 069 B1, which is incorporated herein in its entirety by reference. The isomerization step can be optimized by using an enzymatic procedure. The isomerization can be catalyzed by an isomerase or by a non-enzymatic isomerization factor. For example, the isomerase can be a 3Z:2E-enal isomerase. See, e.g., Noordermeer et al. (1999), which is incorporated herein in its entirety by reference.

Also disclosed are methods of preparing n-hexanal, 3-(Z)-hexen-1-al, 2-(E)-hexen-1-al, or their corresponding alcohols from (9Z, 11E, 13S) 13-hydroperoxyoctadeca-9,11-dienoic acid or (9Z, 11E, 13S, 15Z) 13-hydroperoxyoctadeca-9,11,15-trienoic acid, comprising the steps of contacting the (9Z, 11E, 13S) 13-hydroperoxyoctadeca-9,11-dienoic acid or (9Z, 11E, 13S, 15Z) 13-hydroperoxyoctadeca-9,11,15-trienoic acid with the disclosed 9-BPLs, thereby converting the (9Z, 11E, 13S) 13-hydroperoxyoctadeca-9,11-dienoic acid into n-hexanal or the (9Z, 11E, 13S, 15Z) 13-hydroperoxyoctadeca-9,11,15-trienoic acid into 3-(Z)-hexen-1-al; and either recovering the n-hexanal or 3-(Z)-hexen-1-al; reducing the n-hexanal into n-hexanol or the 3-(Z)-hexen-1-al into 3-(Z)-hexen-1-ol and recovering the hexanol or 3-(Z)-hexen-1-ol; or isomerizing the 3-(Z)-hexen-1-al under temperature and pH conditions effective to obtain 2-(E)-hexen-1-al and either recovering the formed 2-(E)-hexen-1-al or reducing the 2-(E)-hexen-1-al to 2-(E)-hexen-1-ol and recovering the 2-(E)-hexen-1-ol from the medium. The reducing step is preferentially carried out using the enzyme catalyzed reduction described above, and the isomerization step can be optimized using the enzymatic procedure described above.

The present invention is more particularly described in the following examples which are intended as illustrative only since numerous modifications and variations therein will be apparent to those skilled in the art.

EXAMPLES

Example 1

Cloning of Partial cDNAs of Melon Lyases, Including 9-hydroperoxide Lyase

A homology-based cloning method was used to isolate muskmelon (*Cucumis melo*). Generally, the melon mRNA was prepared, reverse transcriptase was used to convert melon mRNA to cDNA. This cDNA was the substrate for the polymerase chain reaction (RT-PCR) using degenerate primers designed to match consensus sequences in the cytochrome P450 family 74 (CYP74). This PCR provided the partial cDNA clones having sequence homology to the CYP74 gene family. The partial clones were extended by 3'-RACE (Rapid Amplification of cDNA Ends) and 5'-RACE reactions, which gave the complete cDNA (i.e., the full complement of mRNA) for each partial clone. The fall length cDNA(s) were cloned by PCR, and expressed in *E. coli*. The catalytic activities of the *E. coli* expressed product was characterized using 9-hydroperoxy and 13-hydroperoxy fatty acids as substrates.

A. Preparation of Melon RNA

The starting material was Cantaloupe melon ("muskmelon"), *Cucumis melo*, of the variety, Caravelle (Asgrow, Tex.). A TRI REAGENT kit (Molecular Research Center, Cincinnati, Ohio) was used to isolate the total RNA. Total RNA was prepared from 20 g of immature melon fruit. 400 μg of total RNA were obtained. An mRNA purification kit (Pharmacia Biotech, Piscataway, N.J.) was used to purify the mRNA from total RNA. The kit provides oligo(dT)-cellulose spin columns for the affinity purification of polyadenylated RNA. The manufacturer's protocol was followed. 3.7 μg of mRNA was isolated from 400 μg of total RNA.

B. RT-PCR Cloning Using Degenerate Primers Based on Conserved CYP74 Sequences

Figure 2A:
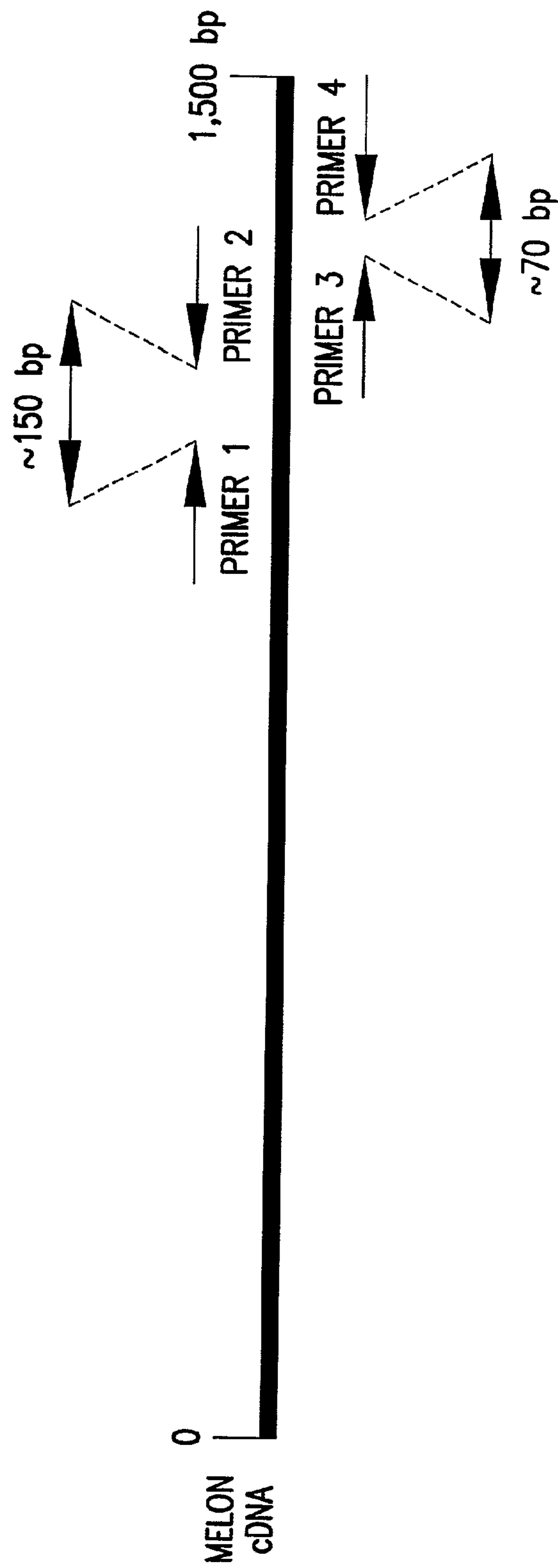
FIG. 2A is a schematic showing the melon cDNA and the regions where the degenerate primers, based on other HPLs and AOSs, bound to produce both the 150 bp and 70 bp cloned products from melon.
Figure 2B:
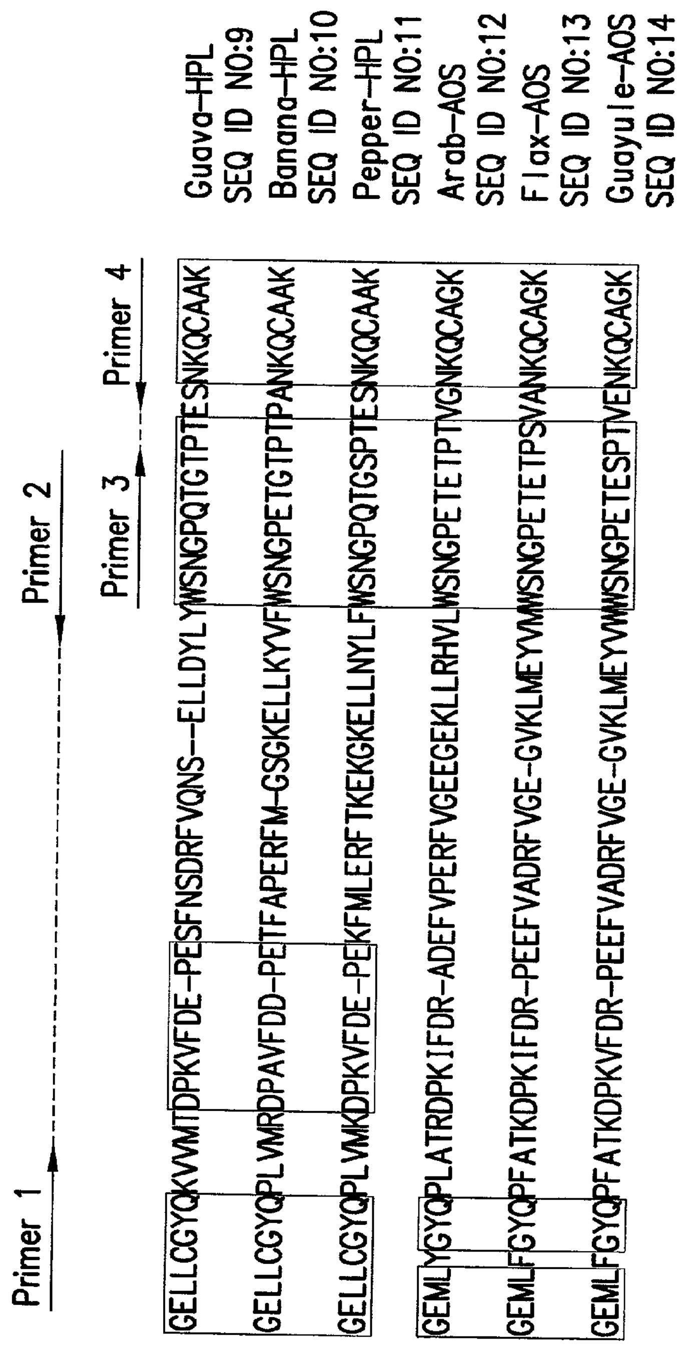
FIG. 2B shows an alignment of partial amino acid sequences from Guava-HPL, Banana-HPL, Pepper-HPL, Arab-AOS, Flax-AOS, and Guayule-AOS. The boxed regions represent areas of high homology among HPLs and AOSs.

First strand cDNA was synthesized from total RNA or poly(A)+RNA using an oligo-d(T)-adaptor. The reverse transcriptase reaction contained 80 pmoles of oligo-dT adaptor (SEQ ID NO: 49, A 1678, 5'-ATG AAT TCG GTA CCC GGG ATC CTT TTT TTT TTT TTT TTT-3' or SEQ ID NO:50, A 1677, 5'-ATG AAT TCG GTA CCC GGG ATC-3'), 10 μl of 5× first strand buffer (GibcoBRL, Rockville, Md.), 1 mM DTT, 1 mM for each dNTP, 50 units RNAsin, 400 U MMV-RT, and $H_2O$ to a final reaction volume of 50 μl. This RT reaction mixture was incubated at 37° for one hour. The first strand cDNA was used directly in PCR reactions without further purification. The PCR reaction contained 20–100 ng of melon cDNA template, 200 μM of each dNTP, 10 mM Tris HCl pH 8.3, 50 mM KCl, 3 mM $MgCl_2$, 20 pmoles of upstream primer (GGTGAGTTGCTNTGYGGNTAYCA (SEQ ID NO:16), GGTGAGTTGCTNTGYGGNTA (SEQ ID NO:17), or TACTGGTCNAAYGGNCCNSARAC (SEQ ID NO:19)) and 20 pmoles of downstream primer (TGGTCNAAYGGNCCRGAGAC (SEQ ID NO:18), AAYAARCARTGYGCNGCTAAGGAC (SEQ ID NO:20), or AARCARTGYGCNGCTAAGGAC (SEQ ID NO:21) (See FIGS. 2 and 3). The PCR reaction further contained 1.25 units of enzyme and $H_2O$ to a final reaction volume of 50 μl. The cDNA template was added when the reaction temperature was 80° C. The reaction cycle parameters were 94° C. for 2 minutes (cycle 1 only); 57° to 62° C. for 1 minute, 72° C. for one minute, 94° for one minute (typically 30 cycles); and 72° C. for 10 minutes (last cycle). The reaction conditions were the same for all reactions, but two different DNA polymerases were used: (1) AmpliTaq DNA polymerase (PE Applied Biosystems, Focter City, Calif.) and (2) AdvanTaq (Advantage cDNA Polymerase Mix (Clontech, Palo Alto, Calif.)).

i. Amplification of the 150 bp cDNA Fragment

A single cycle PCR was performed using melon cDNA as the template. The upstream degenerate primer (SEQ ID NO:16, primer 1A, FIGS. 2 and 3) was used with the dowmstream degenerate primer (SEQ ID NO:18, primer 2, FIGS. 2 and 3), but no band was obtained in this first PCR. Thus, a second PCR was performed using 0.1 μl of the first round PCR reaction products as template, and using the upstream degenerate primer 1B (SEQ ID NO:17, FIGS. 2 and 3) as a nested upstream primer. This second PCR produced a product that migrated as a unique band (150 bp) in an agarose gel. The 150 bp PCR product is comparable in size to the expected Cyp74 gene family product.

The 150 bp product was subcloned into a vector (pCR2.1 by Invitrogen, Carlsbad, Calif.), and about 50 clones were sequenced. Three different P450-related sequences were obtained (FIG. 4), and these were designated partial Clone A (SEQ ID NO:28), Clone B (SEQ ID NO:29), and Clone C (SEQ ID NO:30). Partial clones A and B have 65% identity homology; partial clones A and C have 57% identity homology; and partial clones B and C have 72% identity homology.

ii. Amplification of the 70 bp cDNA Fragment

The single cycle PCR was performed using melon cDNA as template. The upstream degenerate primer (SEQ ID NO:18, Primer 2, FIGS. 2 and 3) was used with a downstream degenerate primer (SEQ ID NO:20, primer 4A, FIGS. 2 and 3). No product band was observed in an agarose gel. Thus, a second PCR was performed using 0.1 ml of the first PCR as template. The downstream degenerate primer, primer 4B, (SEQ ID NO:21, FIGS. 2 and 3) was used as a nested upstream primer. This second PCR produced a product that migrated as a unique band of about 70 bp in an agarose gel. This is comparable in size to the expected product. As the size of this 70 bp band was hard to determine exactly on agarose gels, individual clones (48 clones) were sized by polyacrylamide gel electrophoresis (PAGE) on a 10% gel, using a 10 bp DNA ladder for calibration. The PAGE indicated that a complex mixture of products (60–90 bps) was amplified. Twelve clones close to the predicted size were sequenced. One of these clones encoded a P450-like sequence. This partial clone represented a different region of the 150 bp partial clone B.

Example 2

Generation of Full Length Clones Using 3'-RACE and 5'-RACE Derived Primers

The 3'-RACE (3'-Rapid Amplification of cDNA Ends) method utilizes a degenerate upstream primer for PCR, and a downstream primer based on the adaptor sequence at the 5'-end of the primer used in the reverse transcriptase-catalyzed synthesis of the cDNA. The cDNA was prepared as described in Example 1.

The Marathon cDNA Amplification Kit (Clontech) was used for the 5'-RACE (5'-Rapid Amplification of cDNA Ends). This procedure is designed to convert mRNA (1 μg) into double stranded cDNA and tag the cDNA ends with an adaptor sequence cassette. The protocol followed was that of the manufacturer.

A. 3'-RACE

The cDNA was prepared as described above. Three different preparations of total RNA were used: (1) from the mix of juicy flesh and hard rind of the melon, (2) from the hard rind of the melon, (3) from the juicy flesh of the melon. A gene-specific upstream primer of clone A (5'-GGTTATCAGCCGCTGGTGATG-3' (SEQ ID NO:34) or 5'-ATGAACCGGAGGCGTTAATCCG-3' (SEQ ID NO:35)), B (5'-ACAGAGCGGACGAGTTCGTACCT3' (SEQ ID NO:36)) or C (5'-AGGATTCGGAGAAGTTCGTGGGC-3' (SEQ ID NO:37)) was used with a downstream primer based on the oligo dT-adaptor sequence (SEQ ID NO:49 and 50).

To isolate the full length clones of clone B and C, the gene specific primers for clone B (SEQ ID NO:36) and for clone C (SEQ ID NO:37) and the primer based on the adaptor sequence of the oligo-dT primer (SEQ ID NO:50) were used. The PCR was primed with the cDNA template obtained from the RNA isolated from the mix of juicy flesh and hard rind of the melon. PCR reactions using these primers produced a 350 bp (clone B) product and a 550 bp product (clone C) that migrated as unique bands on an agarose gel.

These 350 and 550 bp PCR products were comparable in size to the expected product from the amplification of the 3'-end of the AOS and 13-HPL cDNAs. These products were subcloned into pCR2.1 and sequenced.

To isolate the fill length clone of clone A, the PCR was primed with the juicy flesh or hard rind melon cDNA template. The gene-specific upstream primer for clone A (SEQ ID NO:34 or SEQ ID NO:35) and a downstream primer based on the oligo dT-adaptor sequence (SEQ ID NO:50) were used for amplification. When the PCR reaction was primed with the hard rind melon cDNA, no PCR product was obtained as determined by agarose gel electrophoresis. When the PCR reaction was primed with the juicy flesh melon cDNA, however, two products were obtained that migrated as unique bands on an agarose gel. The product produced with the primer having the nucleotide sequence of SEQ ID NO:34 was 450 bp and the product produced with the primer having the nucleotide sequence of SEQ ID NO:35 was 400 bp. The difference in size of these two PCR products (50 bp) matched the expected distance between the two upstream primers corresponding to SEQ ID NO:34 and SEQ ID NO:35.

The 400 and 450 bp PCR products produced from primers derived from clone A were comparable in size to the expected product from the 3'-end of the AOS and 13-HPL cDNAs. These products were subdloned into pCR2.1 and sequenced.

Figure 5:
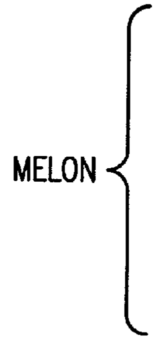
FIG. 5 compares the identities between the partial amino acid sequences encoded by the 3' ends of Clones A, B and C from melon and the C-terminal sequences of 13-HPL from guava, pepper and banana and AOS from flax, guayule, and Arabidopsis. The C-terminal sequences encoded by Clone A and B have 42% identity, whereas clone A and C have 40% and B and C have 49% identity.

FIG. 5 compares the identities between the C-terminal sequences of the amino acid sequences encoded by Clones A, B and C from melon and the C-terminal sequences of 13-BPL from guava, pepper and banana and AOS from flax, guayule, and *Arabidopsis*. This alignment shows that clone A has the most homology with the 13-HPL sequences. Clone B and C have more homology with AOS than with 13-HPL.

Clone B is more like AOS than clone C, and, therefore, clone C is the most divergent from either the AOS or 13-HPL.

B. 5'-RACE

Total RNA was prepared from the juicy flesh melon as described above. The cDNA synthesis for 5'-RACE was accomplished using the Clonetech procedure (Marathon cDNA Amplification Kit). The protocol followed was that of the manufacturer. 1 μg of the mRNA from immature melon fruit was used. A first PCR was performed with melon cDNA as template which was tagged with the Marathon adaptor sequence at the 5' and 3'-ends. The upstream primer AP1 was used with a gene-specific downstream primer (5'-CCG TCA GCA CCA CCA AAT CCT TC-3' (SEQ ID NO:39)) for clone A, 5'-CTG AAC CGA CCG CGA CTG TGT-3' (SEQ ID NO:41) for clone B, and 5'-TCC GCG TCG GCT CCA CTG TC-3' (SEQ ID NO:43) for clone C). A product, which migrated as a diffuse smeared band on an agarose gel, was obtained in this first PCR for each clone. A second PCR was performed using 0.05 μl of the first PCR products as template (a 50 μl PCR reaction). The upstream primer was the adaptor AP2 (Marathon cDNA Amplification Kit) and the downstream gene-specific primer was either 5'-GAA CAG ATA ATC CAG CAG GGC-3' (SEQ ID NO:40) for clone A, 5'-TCG CCC GTG AAC CGA TCA GGT A-3' (SEQ ID NO:42) for clone B, or 5'-TCT CCC ACG AAC CTA TCG CCC A-3' (SEQ ID NO:44) for clone C. This second PCR produced a 1000 bp product for clone A, a 1400 bp product for clone B, and a 1200 bp product for clone C. The 1000 bp, 1400 bp and 1200 bp PCR products are comparable in size to the expected product based on the size of the AOS and 13-HPL cDNAs. These products were subcloned into a vector (pCR2.1, Invitrogen) and sequenced.

After sequencing the 5' and 3'-RACE products of clones B and C, gene-specific primers were synthesized corresponding to the putative start of the coding sequence and at the stop codon. For Clone B, NcoI and EcoRI restriction sites (unique sites) were incorporated at the 5' and 3'-ends respectively using the following primers 5'-GCC ATG GCC TCC ATT GTC ATT CCT TC-3' (SEQ ID NO:45) (NcoI site in bold and bold ATG codes for MET) (5'-up) and 5'-GGA ATT CTT AGT GAT GGT GAT GGT GAT GGA AAC TTG CTT TCT TTA G-3' (SEQ ID NO:46) (EcoRI site in bold and AGT codon represents stop codon) (3'-down).

For clone C, unique NdeI and ClaI restriction sites were incorporated at the 5' and 3'-ends respectively, using the following primers 5'-GCA TAT GGC TAC TCC TTC TTC CTC CTC-3' (SEQ ID NO:47) (NdeI site in bold and bold ATG codes for MET) (5'-up) and 5'-CAT CGA TTT AGT GAT GGT GAT GGT GAT GAT TAG TCA TTA GCT TTA A-3' (SEQ ID NO:48) (ClaI site in bold and AGT is a stop codon) (3'-down). A NcoI site is present in the coding sequence.

The PCR reaction was primed with the melon cDNA prepared from 1 μg of mRNA (as described above) and using either the primer having the nucleotide sequence of SEQ ID NO:45 and the primer having the nucleotide sequence of SEQ ID NO:46 or the primer having the nucleotide sequence of SEQ ID NO:47 and the primer having the nucleotide sequence of SEQ ID NO:48 as primers. The annealing temperature for these reactions was 60° C., and the Advantage cDNA polymerase mix by Clontech was used. A 1.6 kb product for clone B and a 1.4 kb product for clone C were amplified. Each of these products was subcloned into a vector (pCR2.1) and sequenced. The nucleotide sequence of clone B is provided as SEQ ID NO:51, and the nucleotide sequence of clone C is provided as SEQ ID NO:7.

The predicted amino acid sequences encoded by the 1.6 kb product of clone B SEQ ID NO:51 (designated melon AOS in FIG. 1 and having amino acid sequence SEQ ID NO:52) and the 1.4 kb product of clone C (designated melon HPL in FIG. 1 and having SEQ ID NO:7) were compared to the amino acid sequences of AOS from flax (SEQ ID NO:53), guayule (SEQ ID NO:54), and arabidopsis (SEQ ID NO:55) and the amino acid sequence of 13-HPL from guava (SEQ ID NO:38), banana (SEQ ID NO:33) and pepper (SEQ ID NO:32). Note that the start of the sequences (encoded by the 5'ends) contain considerable variations in length and in amino acid sequence before all the sequences converge and begin to show close relatedness. Clone B has a very long 5'-end, which accounts for the longer 5'-RACE product compared to Clone C with a comparatively short 5'end.

By sequence comparison of the available 3'-end, Clone A most resembled the known 13-HPL enzymes. Clone B is a melon AOS. Clone C is a melon 9-hydroperoxide lyase.

Example 3

Expression in *E. coli*

Clone B cDNA in pCR2.1 was cut with NcoI and EcoRI and subcloned into the expression vector plasmid pET3d (digested also with NcoI and EcoRI). Clone C cDNA in pCR2.1 was cut with NdeI and ClaI and subcloned into the expression vector plasmid pET3b (digested also with NdeI and ClaI). The two different constructs were used to transform *E. coli*, strain BL21(DE3) to express the gene product of clones B and C. These constructs gave bacterial expression of the native plant sequences with no additional amino acids or other modification of the 5'-ends.

For expression, the transformed BL21 cells were cultured overnight at 37° C. and 280 rpm in LB medium (3 ml, prepared by dissolving tryptone (10 g), yeast extract (5 g), and NaCl (10 g) in 1 liter of water, adjusting the pH to 7.0 and autoclaving). The antibiotic kanamycin (30 mg) was added aseptically after autoclaving. A portion of the resulting culture (0.2 ml) was then transferred to Terrific Broth (TB, 10 ml, prepared by dissolving bacto-tryptone (12 g), bacto-yeast extract (12 g), and glycerol (4 ml) in deionized water (900 ml), autoclaving and then adding a sterile solution (100 ml) containing 50 μg/ml ampicillin, 0.17 M $KH_2PO_4$, and 0.72 M $K_2HPO_4$) and allowed to grow until the optical density at 260 nm ($OD^{260}$) reached 0.6. This culture was used to inoculate 50 ml of TB containing 50 μg/ml of ampicillin, which was then placed at 28° C. and 200 rpm and a heme precursor, δ-aminolevulimic acid (1 mM), was added followed by the inducer IPTG (0.4 mM) one hour later. The induced cultures were left for a further period of time (4 or 16 hours) and the cells harvested by centrifugation (5,000 rpm for 7 min at 4° C.). The precipitated cells were washed by resuspending them in Tris-HCl buffer (50 mM, pH 7.9) followed by recentrifugation as before.

The resulting pellet of cells was resuspended in Tris-acetate buffer (0.1 M, pH 7.6) containing sucrose (0.5 M), EDTA (0.5 mM) and lysozyme (1 mg/ml). After 30 min on ice, the mixture was centrifuged as before to obtain a pellet of spheroplastes. These were resuspended in potassium phosphate buffer (0.1 M, pH 7.6) containing magnesium acetate (6 mM), glycerol (20% v/v) and DTT (0.1 mM) and the mixture left for 10 min at −80° C. Following this, a protease inhibitor was added (PMSF, 1 mM) and the cells sonicated (2×30 seconds). Analysis of the expression products by SDS-PAGE showed barely detectable bands for both Clones B and C. Compared to the control protein produced from vector alone with no cDNA insert, there was less protein, but the bacterial lysates of each gave easily measurable catalytic activity. By monitoring the disappearance of the UV-235 nm absorbance of the fatty acid hydroperoxide substrates, less than 1 μl (<10 μg crude protein) of the suspended and lysed bacterial pellets were required in order to observe reaction in a 1 ml UV cuvette.

Example 4

Partial Purification of the 9-HPL Derived from Clone C

The 9-HPL enzyme was expressed in *E. coli* (BL21 cells), as discussed in Example 3, however, a His-6 tag was expressed on the carboxyl terminus of the protein using the nucleotide sequence of SEQ ID NO:31. The preparations of solubilized spheroplastes from three 50 ml bacterial cultures were pooled and applied to a nickel-NTA column (purchased from Qiagen) according to the manufacturer's instructions. The column (bed volume 1 ml) was washed with the application buffer (containing 50 mM glycine and 0.1% Emulphogen) and the enzyme was then eluted using the application buffer containing 40 mM histidine and 0.1% Emulphogen detergent. The pooled fractions were subsequently dialyzed overnight to remove the histidine. This gave approximately 5 ml of solution, which by analysis on SDS-PAGE, contained the expected 55 kD band of the 9-HPL as the main protein component. The UV-visible spectrum of the partially purified 9-HPL showed a main Soret band of the hemoprotein with an absorbance of 0.35 AU at 416 nm.

Example 5

Catalytic Activities of the Expressed Melon Clone C

A. Turnover Number of the 9-HPL Using 9S-hydroperoxylinoleic Acid, at Room Temperature, pH 7.6

Measurement was made using the spectrophotometric assay (decrease in absorbance at 235 nm) and the initial rates of reaction. The turnover number of the purified 9-HPL enzyme (number of product molecules formed per molecule of enzyme) using 9S-hydroperoxylinoleic acid as substrate was calculated from the known concentration of the enzyme (measured at the Soret maximum at 416 nm, and using a molar extinction coefficient of 100,000), and the measured rates of change of substrate concentration (using the molar extinction coefficient of 23,000 at 235 nm of the conjugated diene). The values obtained were 3000 turnovers per second for the most active preparation of the 9-HPL enzyme.

This calculation refers to the observed initial rates of reaction. The rates decreased with time as the enzyme undergoes a turnover-dependent inactivation.

B. Identification of Products Formed by the Purified 9-HPL Enzyme from 9S-hydroperoxylinoleic Acid The purified enzyme (approximately 0.4 μg in 2 μl) was reacted with 3 μg [U-14C]9S-hydroperoxylinoleic acid in 100 μl of buffer (potassium phosphate, 0.1 M, pH 7.6). After 30 seconds at room temperature, at which time reaction was complete, methanol (200 μl) was added. The solution was mixed, briefly spun in a bench-top centrifuge, and the supernatant injected on HPLC.

The HPLC system used a Beckman Ultrasphere 5 μm ODS column (25×0.46 cm), a solvent of methanol/water/glacial acetic acid (75/25/0.01, v/v/v), and a flow rate of 1.1 ml/min. The column was coupled to a Hewlett-Packard 1040A diode array detector for detection of UV absorbing compounds, and then the eluant was passed through a Packard Flo-One radioactive on-line detector for recording the profile of $^{14}C$ metabolites.

The substrate, uniformly labeled with $^{14}C$, was converted to two main radiolabeled products, which were equal in area. The early eluting product (at 3.5 min retention time was identified subsequently by GC-MS as 9-oxo-nonanic acid (see below); this product represents the first 9 carbons of the 18 carbon substrate. The second main product, at a retention time of 9 min, coincided precisely in retention time with 3Z-nonenal. This product represents carbons 10–18 of the substrate. A very small back shoulder on this peak, approximately 5% of the peak area, coincided with authentic 2E-nonenal.

C. Identification of 9-oxo-nonanic Acid

The early eluting product (3.5 min retention time) from reaction of the 9-HPL with 9S-hydroperoxylinoleic acid exhibited only weak end absorbance in the UV. This product was purified using the HPLC system described above and was extracted from the column solvent with diethyl ether. An aliquot was redissolved in 20 μl of methanol and treated with ethereal diazomethane to convert the free acid to the methyl ester. Part of this methylated sample was also converted to the methoxime derivative by treatment of the sample with 2% methoxylamine hydrochloride (MOX) in pyridine.

The two samples (methyl ester and methyl ester-methoxime derivatives) were analyzed by GC-MS (gas chromatography-mass spectrometry) operated in the electron impact mode using a Finnigan Incos 50 mass spectrometer coupled to a Hewlett-Packard 5890 gas chromatograph equipped with a SPB-5 fused silica capillary column (30 m ×0.25 mm internal diameter). Samples were injected at 50° C. and the temperature was subsequently programmed to 300° C. at 10°/min. Under these conditions, 9-oxo-nonanic acid methyl ester eluted at 13 minutes retention time. The mass spectrum showed characteristic fragments at m/z 185 (M+-H), 158 (M+-CO), 155 (M+-$OCH_3$), 143 (M+-$CH_2CHO$), 111 and the methyl ester McLafferty fragment ions at m/z 74 and 87. MOX-derivatization of the methyl ester yielded a double gas chromatographic peak comprised of the syn- and anti-oxime isomers which eluted together at about 14.5 minutes. Their mass spectra showed the same main fragment ions with slight differences in ion intensities. Major ions were detected at m/z 215 (M+), 184 (M+-$NH_2OCH_3$), 152 (M+-$NH_2OCH_3$—$CH_3OH$) 124 (184-$CH_3CO_2H$) and 73 ($CH_3$—CNH—$OCH_3$+).

D. Identification of 3Z-nonenal

A reaction of 9S-hydroperoxylinoleic acid with the purified 9-HPL was extracted with hexane and an aliquot of the hexane extract was injected on the GC-MS system described above. Two peaks eluted on GC-MS at the retention times of authentic standards of 3Z-nonenal (≈8 minutes) and 2E-nonenal (≈9 minutes). As judged by peak area, the two aldehydes were formed in a ratio of 10:1 of 3Z to 2E. For identification of the two aldehydes, a standard of 3Z-nonenal was chemically synthesized (see Example 6), and 2E-nonenal was purchased from Aldrich (Milwakee, Wis.). The mass spectra for both aldehydes produced by the 9-HPL reaction with 9S-hydroperoxylinoleic acid are virtually identical with the authentic standards. 3Z-Nonenal shows characteristic fragment ions at m/z 140 (M+), 122 (M+-$H_2O$) and 111 (M+-CHO)), while 2E-nonenal showed ions at m/z 139 (M+-H), 122 (M+-$H_2O$) and 111 (M+-CHO).

Example 6

Chemical Synthesis of 3Z-nonenal 3Z-nonenal synthesis was carried out by slight modifications of the methods of Corey and Suggs (1975), and Andre and Funk (1986). Briefly, to a NaOAc-buffered solution of pyridiniumchlorochromate in methylene chloride, 3Z-nonenol dissolved in methylene chloride was added. After stirring at room temperature, the reaction was terminated by addition of diethyl ether and immediately filtered through a column of silica gel eluted with methylene chloride to remove the oxidizing agent. TLC analysis indicated that conversion to 3Z-nonenal was about 50% complete. The crude product was isolated by open bed column chromatography and purified by RP-HPLC. At all steps during purification, care was taken to prevent oxidation of 3Z-nonenal to 4-hydroperoxy-2E-nonenal. A GC-MS analysis of the chemically synthesized 3Z-nonenal showed that the mass spectrum of the chemically synthesized 3Z-nonenal is virtually identical with the authentic standard, showing the characteristic fragment ions.

Example 7

Figure 6:
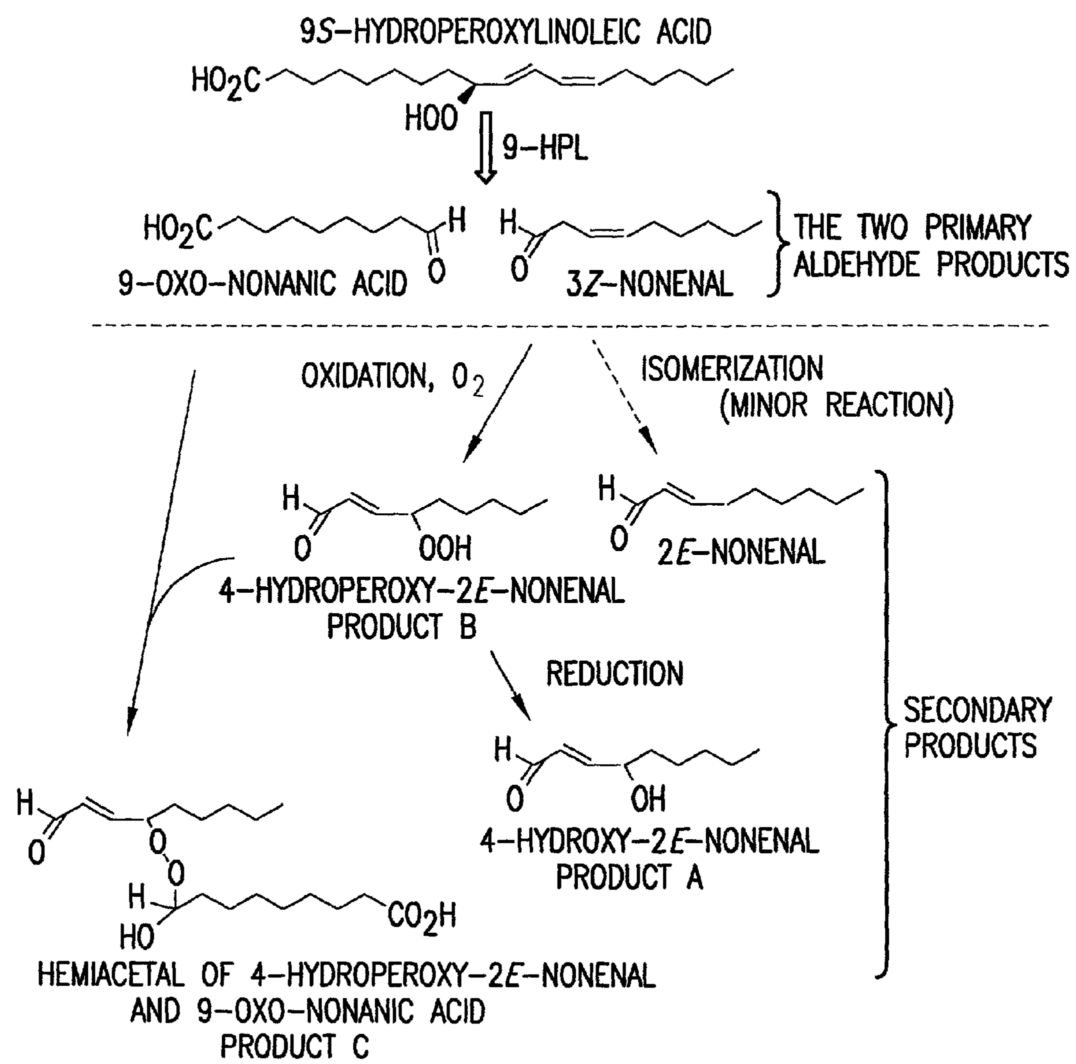
FIG. 6 shows a schematic of the two primary enzymatic products of 9S-hydroperoxyiinoleic acid in the presence of melon 9-HPL: 9-oxo-nonanic acid and 3Z-nonenal. Also depicted is the minor isomerization reaction of 3Z-nonenal to 2E-nonenal, that is observed to a small extent using either the purified enzyme or the crude bacterial lysate. Also depicted is the oxidation reaction that occurs with the crude bacterial lysate, whereby, 3Z-nonenal is oxidized to a mixture of three aldehydes, 4-hydroxy-2E-nonenal (4-HNE), and 4-hydroperoxy-2E-nonenal (4-HPNE), and a hemiacetal derivative formed between 9-oxo-nonanic acid and 4-hydroperoxy-2E-nonenal (hemiacetal).

Identification of Products Formed by the 9-HPL Enzyme in the Crude Bacterial Lysate from 9S-hydroperoxylinoleic Acid When the crude lysate of the bacterial expression was used as a source of 9-BPL we obtained a different product profile compared to that obtained using the purified enzyme. The analytical studies described below (particularly the trapping experiment) led to the conclusion that the initial enzymatic products were identical to those characterized using the purified enzyme. However, in the crude bacterial lysate, one of the two primary enzymatic products, 3Z-nonenal, is readily oxidized (probably non-enzymatically) to a mixture of three aldehydes comprised of 4-hydroxy-2E-nonenal (4-HNE), 4-hydroperoxy-2E-nonenal (4-HPNE), and a hemiacetal derivative formed between 9-oxo-nonanic acid and 4-hydroperoxy-2E-nonenal (hemiacetal). The structures of the three polar aldehydes and their formation from 3Z-nonenal are depicted in FIG. 6. This also shows the minor isomerization of 3Z-nonenal to 2E-nonenal which is observed to a small extent using either the purified enzyme or the crude bacterial lysate. In the crude bacterial lysate, the other primary 9-HPL product, 9-oxo-nonanic acid, is recovered mainly unchanged. A small fraction is converted to the hemiacetal as depicted in FIG. 6.

Using the crude bacterial lysate expressing the melon 9-HPL, reactions with 9S-hydroperoxylinoleic acid were monitored using an oxygen electrode (the electrode records $O_2$ concentration in solution versus time). It was observed by conducting incubations in the closed 2 ml cell of the oxygen electrode that reactions of the 9-HPL from the crude lysate with 9S-hydroperoxylinoleic acid were associated with a fall in $O_2$ concentration in the solution. This reduction in the $O_2$ concentration corresponds to the reaction of $O_2$ with 3Z-nonenal to give the three polar aldehydes. Quantitatively, the fall in $O_2$ concentration (nmole $O_2$ consumed) corresponded approximately to the nmole of polar aldehyde derivatives detected by HPLC analysis. By contrast to the crude enzyme preparation, reactions of the purified 9-HPL with 9S-hydroperoxylinoleic acid were associated with no change in $O_2$ concentration in solution.

Using the crude bacterial lysate expressing the melon 9-HPL, reactions with 9S-hydroperoxylinoleic acid were monitored either using the $O_2$ electrode or spectrophotometrically at 235 nm as described above. The solutions were then extracted using a C18 extraction cartridge (Bond-Elut from Varian), and eluted using diethyl ether. The ether extracts were evaporated to dryness and analyzed by HPLC. The profile of radiolabeled products was obtained using [1-$^{14}$C]9S-hydroperoxylinoleic acid ($^{14}$C on carbon-1) and [U-$^{14}$C]9S-hydroperoxylinoleic acid ($^{14}$C uniformly on all 18 carbons) as substrate. The profile of UV-absorbing materials was detected by monitoring at 205 mn and 220 mn. When using 1-$^{14}$C substrate, only products retaining carbon-1 of the substrate are radiolabeled (i.e. 9-oxo-nonanic acid and the hemiacetal product), and from U-$^{14}$C substrate, all products are radiolabeled.

The largest radiolabeled peak, formed from both the 1-$^{14}$C and the uniformly-labeled $^{14}$C substrate, was identified as 9-oxo-nonanic acid. This corresponds to carbons 1–9 of the original substrate and this primary aldehydic product of the 9-HPL is recovered mainly intact from the incubations. A small amount is converted to hemiacetal as shown in FIG. 6.

The three products are derived via the initial oxygenation of 3Z-nonenal. This oxidation of 3Z-nonenal, initially to form 4-hydroperoxy-2E-nonenal (4-HPNE), is probably a non-enzymatic reaction that occurs readily in the crude bacterial lysate. The 4-HPNE is partly reduced to 4-HNE. The 4-HPNE also reacts with 9-oxo-nonanic acid to form the hemiacetal derivative (FIGS. 6).

Example 8

Evidence that the Primary Products of the 9-HPL in the Crude Bacterial Lysate are 9-oxo-nonanic Acid and 3Z-nonenal For this series of experiments, prior to reaction with the crude 9-BPL, the oxygen concentration in the buffer was reduced to zero. This was accomplished by addition of small aliquots of a solution of sodium dithionite while monitoring the $O_2$ concentration using the oxygen electrode.

Using buffer depleted of oxygen, it was shown that the rate of reaction of the 9-HPL with 9S-hydroperoxylinoleic acid was not decreased by the absence of $O_2$. This was demonstrated using the spectrophotometric assay (rate of disappearance of the UV absorbance at 235 nm).

Reaction of [U-$^{14}$C]9S-hydroperoxylinoleic acid (40 μg) with 9-HPL from the crude bacterial lysate was carried out in $O_2$-depleted buffer in the 2 ml cell of the oxygen electrode. After 1 minute, at which time the reaction was expected to be almost complete, 50 μl of a freshly prepared 10 mg/ml solution of $NaBH_4$ was injected and the reduction reaction allowed to proceed for 5 minutes. This procedure immediately reduced (and thereby stabilized) the aldehydes as the corresponding alcohols (9-hydroxy-nonanic acid and 3Z-nonenol).

The 2 ml solution was subsequently extracted using a C18 extraction cartridge (Bond-Elut, from Varian) and the products recovered by elution with diethyl ether. 50 μg of unlabeled authentic 3Z-nonenol and 50 μg 2E-nonenol (obtained from Aldrich) were added to an aliquot of the sample and the sample was then analyzed by HPLC.

One chromatogram showed the radiolabeled products and another chromatogram depicted the UV profile at 205 mn. The two main peaks in the UV chromatogram corresponded to the two added standards and thus establish the precise retention times of 3Z-nonenol and 2E-nonenol. The later peaks in the UV chromatogram correspond to the reduction product of unused substrate (9-hydroxy-linoleic acid) and its 10trans-12trans isomer that may have been a minor contaminant of the original substrate.

The $^{14}$C chromatogram showed an early eluting peak at 3 minutes identified as 9-hydroxy-nonanic acid, the $NaBH_4$-reduction product of the primary enzymatic product, 9-oxo-nonanic acid. The second main radiolabeled peak, eluting at 8.8 minutes, corresponded to 3Z-nonenol, the $NaBH_4$-reduction product of 3Z-nonenal. 2E-Nonenol was not detected in the $NaBH_4$-trapping experiment. This suggested that the corresponding aldehyde, 2E-nonenal, was not a primary enzymatic product, but rather was formed by non-enzymatic isomerization. In the $NaBH_4$-trapping experiment, its formation was reduced due to the prompt conversion of the 3Z-nonenal to the more stable alcohol.

The results of the trapping experiment indicate that the activity of the 9-HPL in the crude bacterial lysate was restricted to conversion of 9S-hydroperoxy-linoleic acid to the two primary aldehydes, 9-oxo-nonanic acid and 3Z-nonenal. The other aldehydes recovered from reactions of the 9-HPL in the crude bacterial lysate were formed by subsequent reactions of the primary products with molecular oxygen or by isomerization to 2E-nonenal.

Example 9

Identification of 4-hydroperoxy-2E-nonenal (4-HPNE) and 4-hydroxy-2E-nonenal (4-HNE)

From the incubations described in Example 7, 4-HPNE was isolated by reversed-phase HPLC and characterized by $^1$H-NMR spectroscopy (9.58 ppm, d, J=7.8, H1; 6.9 ppm, dd, J=15.9, 6.2, H3; 6.25, ddd, J=15.9, 7.8, 1.2, H2; 4.6 ppm, q (with some fine structure), J>>6.5, H4). Formation of 4-hydroxy-2E-nonenal (4-HNE) was also seen in the bacterial lysate reactions where it was formed by non-specific reduction of 4-HPNE (see Example 7). The 4-HNE recovered from enzyme incubations was identical in its UV spectrum and HPLC retention times to an authentic sample of 4-HNE obtained from Cayman Chemical Co. (Ann Arbor, Mich.).

For mass spectrometric characterization of 4-HPNE, an aliquot was reduced using triphenyphosphine to the corresponding alcohol, 4-HNE and repurified by HPLC. Using the previously described GC-MS system, the 4-HNE was analyzed directly and after treatment with BSTFA to give the trimethylsilyl ether derivative. The fragment ions obtained for the non-derivatized 4-HNE are in accord with reports in the literature (Gardner et al., 1992). Specifically, the following fragment ions were observed: m/z 138 (M+-$H_2O$), 127 (M+-CHO), 109 (M+-CHO—$H_2O$), 99, 86, and 85. The trimethylsilyl ether derivative showed diagnostic ions at m/z 199 (M+-CHO), 157 (CHO—$C_2H_2$—CH—OSi($CH_3$)3+) and 129 (CHO—$C_2H_2$—CH—OSi($CH_3$)3+-CO).

Throughout this application, various publications are referenced. The disclosures of these publications in their entireties are hereby incorporated by reference into this application in order to more fully describe the state of the art to which this invention pertains.

REFERENCES

1. Andre, J. C., and Funk, M. O. Jr. (1986) Determination of stereochemistry in the fatty acid hydroperoxide products of lipoxygenase catalysis. Anal. Biochem. 158, 316–321.
2. Baneji, J. L. et al. (1983) A lymphocyte-specific cellular enhancer is located downstream of the joining region in immunoglobulin heavy chain genes. Cell 33: 729–40.
3. Corey, E. J., and Suggs, J. W. (1975) Pyridinium chlorochromate. An efficient reagent for oxidation of primary and secondary alcohols to carbonyl compounds. Tetrahedron Lett. 31, 2647–2650.
4. T. E. Creighton (1983), Proteins: Structure and Molecular Properties, W. H. Freeman & Co., San Francisco pp 79–86.
5. Fauconnier, M. L., Perez, A. G., Sanz, C., Marlier, M. (1997). Purification and Characterization of Tomato Leaf (*Lycopersicon esculentum* Mill.) Hydroperoxide Lyase. J. Agric. Food Chem. 45:4232.
6. Gardner, H. W., Bartelt, R. J., and Weisleder, D. (1992) A facile synthesis of 4-hydroxy-2(E)-nonenal, Lipids 27, 686–689.
7. Hornostaj A R and Robinson D S (1998) Purification of hydroperoxide lyase from cucumber, Food Chemistry 66:173–180.
8. Itoh and Vick (1999) The purification and characterization of fatty acid hydroperoxide lyase in sunflower, Biochim Biophys Acta. 1436:531–40.

9. Kim, I. S. and Grosch, W. (1981) Partial purification of a hydrogenperoxide lyase from fruits of pear. J. Agri. Food Chem. 29:1200–1225.

10. Laimins, L. et al. (1981) Osmotic control of kdp operon expression in *Escherichia coli*. Proc. Natl. Acad. Sci. USA 78:464–68.

11. Lusky, M. L. et al. (1983) Bovine papilloma virus contains an activator of gene expression at the distal end of the early transcription unit. Mol. Cell Biol. 3:1108–22.

12. Matsui K., Shibata Y., Kajiwara, T. and Hatanaka A. (1989). Separation of 13- and 9-hydroperoxide lyase activities in cotyledons of cucumber seedlings. Z. Naturforsch. 44c:883–885.

13. Matsui K, Toyota H., Kajiwara T., Kakuno T. and Hatanaka A. (1991). Fatty acid hydroperoxide cleaving enzyme, hydroperoxide lyase, from tea leaves. Phytochemistry 30:2109–2113.

14. Mulligan, R. C. and Berg P. (1980) Expression of a bacterial gene in mammalian cells. Science. 209:1422–27.

15. Noordermeer et al. (1999) Alfalfa contains substantial 9-hydroperoxide lyase activity and a 3Z:2E-enal isomerase. FEBS Lett. 443:201–204.

16. Verma, I. M. (1985) Retroviral vectors for gene transfer. In Microbiology-1985, American Society for Microbiology, pp. 229–232, Washington.

17. Olias et al. (1990) Fatty acid hydroperoxide lyase in germinating soybean seedlings. J. Agric. Food Chem. 38:624–630.

18. Osborne, T. F., et al. (1984) Transcription control region within the protein-coding portion of adenovirus E1A genes. Mol. Cell Biol. 4:1293–305.

19. Schreier P. and Lorenz G. (1982) Separation, partial purification and characterization of a fatty acid hydroperoxide cleaving enzyme from apple and tomato fruits. Z. Naturforsch 37c:165–173.

20. Shibata Y., Matsui K, Kajiwara T. and Hatanaka, A. (1995). Purification and properties of fatty acid hydroperoxide lyase from green bell pepper fruits. *Plant Cell Physiology* 36:147–156.

21. Southern P. J. and Berg, P. (1982) Transformation of mammalian cells to antibiotic resistance with a bacterial gene under control of the SV40 early region promoter. J. Mol. Appl. Genet. 1:327–41.

22. Sugden, B. et al. (1985) A vector that replicates as a plasmid and can be efficiently selected in B-lymphoblasts transformed by Epstein-Barr virus. Mol. Cell. Biol. 5:410–13.

23. Tressl, R. and Drawert, F. (1973). Biogenesis of banana volatiles. *J. Agric. Food Chem.* 21:560–565.

24. Vick B. A. and Zimmerman D. C. (1976). Lipoxygenase and hydroperoxide lyase in germinating watermelon seedlings. *Plant Physiol.* 57:780–788.

25. Wolff, J. A., et al. (1990) Direct gene transfer into mouse muscle in vivo. Science 247:1465–68.

26. Acsadi, G. (1991) Human dystrophin expression in mdx mice after intramuscular injection of DNA constructs. Nature 352:815–18.

What is claimed is:

1. A method of preparing 3-(Z)-nonenal, 2-(E)-nonenal, or their corresponding alcohols from (9S,10E,12Z) 9-hydroperoxyoctadeca-10,12-dienoic acid, comprising (a) contacting the (9S,10E,12Z) 9-hydroperoxyoctadeca-10,12-dienoic acid with an isolated fatty acid hydroperoxide lyase having activity for both 9-hydroperoxide substrates and 13-hydroperoxide substrates, comprising the amino acid sequence SEQ ID NO:7, wherein the lyase has a 9-HPL function, thereby converting the (9S,10E,12Z) 9-hydroperoxyoctadeca-10,12-dienoic acid into 3-(Z)-nonenal; and either (b) recovering the 3-(Z)-nonenal;

(c) reducing the 3-(Z)-nonenal into 3-(Z)-nonenol and recovering the 3-(Z)-nonenol; or (d) isomerizing the 3-(Z)-nonenal under temperature and pH conditions effective to obtain 2-(E)-nonenal and either recovering the formed 2-(E)-nonenal or reducing the 2-(E)-nonenal to 2-(E)-nonenol and recovering the 2-(E)-nonenol from the medium.

2. The method of claim 1, wherein the lyase has activity for both 9-hydroperoxide substrates and 13-hydroperoxide substrates, wherein $K_m$ and $V_{max}$ of the lyase for 9-hydroperoxylinolenic acid are greater than $K_m$ and $V_{max}$ of the lyase for 9-hydroperoxylinoleic acid.

3. The method of claim 2, wherein the $V_{max}$ of the lyase for 9-hydroperoxide substrates is greater than the $V_{max}$ for 13-hydroperoxide substrates.

4. The method of claim 2, wherein the $K_m$ of the lyase for 9-hydroperoxide substrates is greater than for 13-hydroperoxide substrates.

5. The method of claim 1, wherein the lyase comprises the amino acids unique to *Cucumis melo* and set forth in SEQ ID NO:7 which provide the activity of cleaving 9-hydroperoxide substrates with greater activity than 13-hydroperoxide substrates.

6. A method of preparing n-hexanal or its corresponding alcohol from (9Z,11E,13S) 13-hydroperoxyoctadeca-9,11-dienoic acid, comprising (a) contacting the (9Z,11E,13S) 13-hydroperoxyoctadeca-9,11-dienoic acid with an isolated fatty acid hydroperoxide lyase having activity for both 9-hydroperoxide substrates and 13-hydroperoxide substrates, comprising the amino acid sequence SEQ ID NO:7, wherein the lyase has a 9-HPL function, thereby converting the (9Z,11E,13S) 13-hydroperoxyoctadeca-9,11-dienoic acid into n-hexanal; and either (b) recovering the n-hexanal; or (c) reducing the n-hexanal into n-hexanol and recovering the n-hexanol.

7. The method of claim 6, wherein the lyase has activity for both 9-hydroperoxide substrates and 13-hydroperoxide substrates, wherein $K_m$ and $V_{max}$ of the lyase for 9-hydroperoxylinolenic acid are greater than $K_m$ and $V_{max}$ of the lyase for 9-hydroperoxylinoleic acid.

8. The method of claim 7, wherein the $V_{max}$ of the lyase for 9-hydroperoxide substrates is greater than the $V_{max}$ for 13-hydroperoxide substrates.

9. The method of claim 7, wherein the $K_m$ of the lyase for 9-hydroperoxide substrates is greater than for 13-hydroperoxide substrates.

10. The method of claim 6, wherein the lyase comprises the amino acids unique to *Cucumis melo* and set forth in SEQ ID NO:7 which provide the activity of cleaving 9-hydroperoxide substrates with greater activity than 13-hydroperoxide substrates.

11. A method of preparing (3Z,6Z)-nonadienal, (2E,6Z)-nonadienal, or their corresponding alcohols from (9S,10E,12Z,15Z) 9-hydroperoxyoctadeca-10,12,15-trienoic acid, comprising (a) contacting the (9S,10E,12Z,15Z) 9-hydroperoxyoctadeca-10,12,15-trienoic acid with an isolated fatty acid hydroperoxide lyase having activity for both 9-hydroperoxide substrates and 13-hydroperoxide substrates, comprising the amino acid sequence SEQ ID NO:7, wherein the lyase has a 9-HPL function, thereby converting the (9S,10E,12Z,15Z) 9-hydroperoxyoctadeca-10,12,15-trienoic acid into (3Z,6Z)-nonadienal; and either (b) recovering the (3Z,6Z)-nonadienal;

(c) reducing the (3Z,6Z)-nonadienal into (3Z,6Z)-nonadienol and recovering the (3Z,6Z)-nonadienol; or (d) isomerizing the (3Z,6Z)-nonadienal under temperature and pH conditions effective to obtain (2E,6Z)-nonadienal and either recovering the formed (2E,6Z)-nonadienal or reducing the (2E,6Z)-nonadienal to (2E,6Z)-nonadienol and recovering the (2E,6Z)-nonadienol from the medium.

12. The method of claim 11, wherein the lyase has activity for both 9-hydroperoxide substrates and 13-hydroperoxide substrates, wherein $K_m$ and $V_{max}$ of the lyase for 9-hydroperoxylinolenic acid are greater than $K_m$ and $V_{max}$ of the lyase for 9-hydroperoxylinoleic acid.

13. The method of claim 12, wherein the $V_{max}$ of the lyase for 9-hydroperoxide substrates is greater than the $V_{max}$ for 13-hydroperoxide substrates.

14. The method of claim 12, wherein the $K_m$ of the lyase for 9-hydroperoxide substrates is greater than for 13-hydroperoxide substrates.

15. The method of claim 11, wherein the lyase comprises the amino acids unique to *Cucumis melo* and set forth in SEQ ID NO:7 which provide the activity of cleaving 9-hydroperoxide substrates with greater activity than 13-hydroperoxide substrates.

16. A method of preparing 3-(Z)-hexen-1-al, 2-(E)-hexen-1-al, or their corresponding alcohols from (9Z,11E,13S,15Z) 13-hydroperoxyoctadeca-9,11,15-trienoic acid, comprising (a) contacting the (9Z,11E,13S,15Z) 13-hydroperoxyoctadeca-9,11,15-trienoic acid with an isolated fatty acid hydroperoxide lyase having activity for both 9-hydroperoxide substrates and 13-hydroperoxide substrates, comprising the amino acid sequence SEQ ID NO:7, wherein the lyase has a 9-HPL function, thereby converting the (9Z,11E,13S,15Z) 13-hydroperoxyoctadeca-9,11,15-trienoic acid into 3-(Z)-hexen-1-al; and either (b) recovering the 3-(Z)-hexen-1-al;

(c) reducing the 3-(Z)-hexen-1-al into 3-(Z)-hexen-1-ol and recovering the 3-(Z)-hexen-1-ol; or (d) isomerizing the 3-(Z)-hexen-1-al under temperature and pH conditions effective to obtain 2-(E)-hexen-1-al and either recovering the formed 2-(E)-hexen-1-al or reducing the 2-(E)-hexen-1-al to 2-(E)-hexen-1-ol and recovering the 2-(E)-hexen-1-ol from the medium.

17. The method of claim 16, wherein the lyase has activity for both 9-hydroperoxide substrates and 13-hydroperoxide substrates, wherein $K_m$ and $V_{max}$ of the lyase for 9-hydroperoxylinolenic acid are greater than $K_m$ and $V_{max}$ of the lyase for 9-hydroperoxylinoleic acid.

18. The method of claim 17, wherein the $V_{max}$ of the lyase for 9-hydroperoxide substrates is greater than the $V_{max}$ for 13-hydroperoxide substrates.

19. The method of claim 17, wherein the $K_m$ of the lyase for 9-hydroperoxide substrates is greater than for 13-hydroperoxide substrates.

20. The method of claim 16, wherein the lyase comprises the amino acids unique to *Cucumis melo* and set forth in SEQ ID NO:7 which provide the activity of cleaving 9-hydroperoxide substrates with greater activity than 13-hydroperoxide substrates.

* * * * *

SEQUENCE LISTING

```
<160> NUMBER OF SEQ ID NOS: 56

<210> SEQ ID NO 1
<211> LENGTH: 10
<212> TYPE: PRT
<213> ORGANISM: Cucumis melo

<400> SEQUENCE: 1

Met Ala Thr Pro Ser Ser Ser Ser Pro Glu
 1              5                  10


<210> SEQ ID NO 2
<211> LENGTH: 15
<212> TYPE: PRT
<213> ORGANISM: Cucumis melo

<400> SEQUENCE: 2

Ile Leu Phe Asp Thr Ala Lys Val Glu Lys Arg Asn Ile Leu Asp
 1              5                  10                  15


<210> SEQ ID NO 3
<211> LENGTH: 8
<212> TYPE: PRT
<213> ORGANISM: Cucumis melo

<400> SEQUENCE: 3

Arg Leu Phe Leu Ser Phe Leu Ala
 1              5


<210> SEQ ID NO 4
```

-continued

```
<211> LENGTH: 7
<212> TYPE: PRT
<213> ORGANISM: Cucumis melo

<400> SEQUENCE: 4

Ser Ile Ser Asp Ser Met Ser
 1               5


<210> SEQ ID NO 5
<211> LENGTH: 8
<212> TYPE: PRT
<213> ORGANISM: Cucumis melo

<400> SEQUENCE: 5

Leu Leu Ser Asp Gly Thr Pro Asp
 1               5


<210> SEQ ID NO 6
<211> LENGTH: 10
<212> TYPE: PRT
<213> ORGANISM: Cucumis melo

<400> SEQUENCE: 6

Ile Phe Ser Val Phe Glu Asp Leu Val Ile
 1               5                  10


<210> SEQ ID NO 7
<211> LENGTH: 481
<212> TYPE: PRT
<213> ORGANISM: Cucumis melo

<400> SEQUENCE: 7

Met Ala Thr Pro Ser Ser Ser Ser Pro Glu Leu Pro Leu Lys Pro Ile
 1               5                  10                  15

Pro Gly Gly Tyr Gly Phe Pro Phe Leu Gly Pro Ile Lys Asp Arg Tyr
            20                  25                  30

Asp Tyr Phe Tyr Phe Gln Gly Arg Asp Glu Phe Phe Arg Ser Arg Ile
        35                  40                  45

Thr Lys Tyr Asn Ser Thr Val Phe Arg Ala Asn Met Pro Pro Gly Pro
    50                  55                  60

Phe Ile Ser Ser Asp Ser Arg Val Val Val Leu Leu Asp Ala Leu Ser
65                  70                  75                  80

Phe Pro Ile Leu Phe Asp Thr Ala Lys Val Glu Lys Arg Asn Ile Leu
                85                  90                  95

Asp Gly Thr Tyr Met Pro Ser Leu Ser Phe Thr Gly Asn Ile Arg Thr
            100                 105                 110

Cys Ala Tyr Leu Asp Pro Ser Glu Thr Glu His Ser Val Leu Lys Arg
        115                 120                 125

Leu Phe Leu Ser Phe Leu Ala Ser Arg His Asp Arg Phe Ile Pro Leu
    130                 135                 140

Phe Arg Ser Ser Leu Ser Glu Met Phe Val Lys Leu Glu Asp Lys Leu
145                 150                 155                 160

Ser Glu Lys Lys Lys Ile Ala Asp Phe Asn Ser Ile Ser Asp Ser Met
                165                 170                 175

Ser Phe Asp Tyr Val Phe Arg Leu Leu Ser Asp Gly Thr Pro Asp Ser
            180                 185                 190

Lys Leu Ala Ala Glu Gly Pro Gly Met Phe Asp Leu Trp Leu Val Phe
        195                 200                 205

Gln Leu Ala Pro Leu Ala Ser Ile Gly Leu Pro Lys Ile Phe Ser Val
```

-continued

```
    210                 215                 220

Phe Glu Asp Leu Val Ile His Thr Ile Pro Leu Pro Phe Phe Pro Val
225                 230                 235                 240

Lys Ser Gly Tyr Arg Lys Leu Tyr Glu Ala Phe Tyr Ser Ser Ser Gly
                245                 250                 255

Ser Phe Leu Asp Glu Ala Glu Lys Gln Gly Ile Asp Arg Glu Lys Ala
            260                 265                 270

Cys His Asn Leu Val Phe Leu Ala Gly Phe Asn Ala Tyr Gly Gly Met
        275                 280                 285

Lys Val Leu Phe Pro Thr Leu Leu Lys Trp Val Gly Thr Ala Gly Glu
    290                 295                 300

Asp Leu His Arg Lys Leu Ala Glu Glu Val Arg Thr Thr Val Lys Glu
305                 310                 315                 320

Glu Gly Gly Leu Thr Phe Ser Ala Leu Glu Lys Met Ser Leu Leu Lys
                325                 330                 335

Ser Val Val Tyr Glu Ala Leu Arg Ile Glu Pro Pro Val Pro Phe Gln
            340                 345                 350

Tyr Gly Lys Ala Lys Glu Asp Ile Val Ile Gln Ser His Asp Ser Ser
        355                 360                 365

Phe Lys Ile Lys Lys Gly Glu Thr Ile Phe Gly Tyr Gln Pro Phe Ala
    370                 375                 380

Thr Lys Asp Pro Lys Ile Phe Lys Asp Ser Glu Lys Phe Val Gly Asp
385                 390                 395                 400

Arg Phe Val Gly Glu Glu Gly Glu Lys Leu Leu Lys Tyr Val Tyr Trp
                405                 410                 415

Ser Asn Glu Arg Glu Thr Val Glu Pro Thr Ala Glu Asn Lys Gln Cys
            420                 425                 430

Pro Gly Lys Asn Leu Val Val Leu Ile Gly Arg Ile Met Val Val Glu
        435                 440                 445

Phe Phe Leu Arg Tyr Asp Thr Phe Thr Val Glu Val Ala Asp Leu Pro
    450                 455                 460

Leu Gly Pro Ala Val Lys Phe Lys Ser Leu Thr Arg Ala Thr Asp Met
465                 470                 475                 480

Val
```

```
<210> SEQ ID NO 8
<211> LENGTH: 1446
<212> TYPE: DNA
<213> ORGANISM: Cucumis melo

<400> SEQUENCE: 8

atggctactc cttcttcctc ctcccctgaa cttcctctca aaccaattcc cggtggctat      60

ggcttcccct tcctcggtcc catcaaagac cgttacgatt acttctattt ccaaggtaga     120

gacgaattct tccgttcccg gattaccaaa tacaactcca ccgtcttccg cgccaacatg     180

ccaccgggcc ccttcatttc ctccgattcc agagtcgttg tccttctcga tgccctcagt     240

tttcctatcc tcttcgacac agccaaagtc gagaaacgca acattctcga cggaacttac     300

atgccctcct tgtccttcac cggcaacatt cgcacctgtg cttatttgga cccatcggaa     360

acagagcact ctgttctcaa acgcctcttc ctctcctttc tcgcttcccg ccatgacagg     420

ttcatccctc tgtttcgaag ctccttgtct gagatgtttg ttaagcttga agataaactt     480

tccgagaaaa agaagatcgc tgatttcaac tcgatcagcg attccatgtc gtttgattat     540

gttttccgtt tactctccga tggaacccct gattcgaaat tagctgctga gggacctgga     600
```

-continued

```
atgttcgatc tgtggcttgt gtttcaactc gccccattgg cttccattgg ccttcccaaa    660

attttctctg tttttgaaga tctcgtcatt cacaccattc ccctgccttt cttcccagtc    720

aagagtggtt acaggaagct ttatgaagcg ttttactcct cttctggctc atttctagac    780

gaagcagaga aacaggggat agacagggag aaagcatgtc acaatttagt gtttctcgct    840

ggattcaacg catacggggg aatgaaagtc ctttttccca ctttactgaa atgggtcggc    900

accgccggcg aggatctcca ccggaaactc gccgaggaag tcaggacaac cgtgaaggaa    960

gaagggggac tgactttctc cgccttggag aaaatgagtc tgctgaagtc cgtcgtgtac   1020

gaagcactca ggatcgaacc gccggtgccg ttccagtacg ggaaagcgaa ggaggatatc   1080

gtgattcaga gccacgattc ttctttcaag atcaaaaaag gggagacgat tttggttat   1140

cagccgtttg ctactaaaga tccgaagatt tttaaggatt cggagaagtt cgtgggcgat   1200

aggttcgtgg gagaggaagg ggagaagctt ttgaagtatg tttactggtc aaatgagcgg   1260

gagacagtgg agccgacggc ggagaacaag cagtgtccgg ggaagaatct ggtggtgctg   1320

ataggtagga ttatggtggt ggaattcttc cttcgttatg atacgttcac cgtggaggtc   1380

gcagatttgc cgctgggtcc ggcagtgaag ttcaagtcct taaccagagc aaccgatatg   1440

gtttaa                                                              1446
```

```
<210> SEQ ID NO 9
<211> LENGTH: 60
<212> TYPE: PRT
<213> ORGANISM: Psidium Guava

<400> SEQUENCE: 9

Gly Glu Leu Leu Cys Gly Tyr Gln Lys Val Val Met Thr Asp Pro Lys
 1               5                  10                  15

Val Phe Asp Glu Pro Glu Ser Phe Asn Ser Asp Arg Phe Val Gln Asn
            20                  25                  30

Ser Glu Leu Leu Asp Tyr Leu Tyr Trp Ser Asn Gly Pro Gln Thr Gly
        35                  40                  45

Thr Pro Thr Glu Ser Asn Lys Gln Cys Ala Ala Lys
    50                  55                  60


<210> SEQ ID NO 10
<211> LENGTH: 61
<212> TYPE: PRT
<213> ORGANISM: Banana

<400> SEQUENCE: 10

Gly Glu Leu Leu Cys Gly Tyr Gln Pro Leu Val Met Arg Asp Pro Ala
 1               5                  10                  15

Val Phe Asp Asp Pro Glu Thr Phe Ala Pro Glu Arg Phe Met Gly Ser
            20                  25                  30

Gly Lys Glu Leu Leu Lys Tyr Val Phe Trp Ser Asn Gly Pro Glu Thr
        35                  40                  45

Gly Thr Pro Thr Pro Ala Asn Lys Gln Cys Ala Ala Lys
    50                  55                  60


<210> SEQ ID NO 11
<211> LENGTH: 62
<212> TYPE: PRT
<213> ORGANISM: Capsicum annum (green pepper)

<400> SEQUENCE: 11
```

-continued

```
Gly Glu Leu Leu Cys Gly Tyr Gln Pro Leu Val Met Lys Asp Pro Lys
 1               5                  10                  15

Val Phe Asp Glu Pro Glu Lys Phe Met Leu Glu Arg Phe Thr Lys Glu
            20                  25                  30

Lys Gly Lys Glu Leu Leu Asn Tyr Leu Phe Trp Ser Asn Gly Pro Gln
        35                  40                  45

Thr Gly Ser Pro Thr Glu Ser Asn Lys Gln Cys Ala Ala Lys
    50                  55                  60


<210> SEQ ID NO 12
<211> LENGTH: 62
<212> TYPE: PRT
<213> ORGANISM: Arabidopsis

<400> SEQUENCE: 12

Gly Glu Met Leu Tyr Gly Tyr Gln Pro Leu Ala Thr Arg Asp Pro Lys
 1               5                  10                  15

Ile Phe Asp Arg Ala Asp Glu Phe Val Pro Glu Arg Phe Val Gly Glu
            20                  25                  30

Glu Gly Glu Lys Leu Leu Arg His Val Leu Trp Ser Asn Gly Pro Glu
        35                  40                  45

Thr Glu Thr Pro Thr Val Gly Asn Lys Gln Cys Ala Gly Lys
    50                  55                  60


<210> SEQ ID NO 13
<211> LENGTH: 61
<212> TYPE: PRT
<213> ORGANISM: Flax

<400> SEQUENCE: 13

Gly Glu Met Leu Phe Gly Tyr Gln Pro Phe Ala Thr Lys Asp Pro Lys
 1               5                  10                  15

Ile Phe Asp Arg Pro Glu Glu Phe Val Ala Asp Arg Phe Val Gly Glu
            20                  25                  30

Gly Val Lys Leu Met Glu Tyr Val Met Trp Ser Asn Gly Pro Glu Thr
        35                  40                  45

Glu Thr Pro Ser Val Ala Asn Lys Gln Cys Ala Gly Lys
    50                  55                  60


<210> SEQ ID NO 14
<211> LENGTH: 61
<212> TYPE: PRT
<213> ORGANISM: Guayule

<400> SEQUENCE: 14

Gly Glu Met Leu Phe Gly Tyr Gln Pro Phe Ala Thr Lys Asp Pro Lys
 1               5                  10                  15

Val Phe Asp Arg Pro Glu Glu Phe Val Ala Asp Arg Phe Val Gly Glu
            20                  25                  30

Gly Val Lys Leu Met Glu Tyr Val Trp Trp Ser Asn Gly Pro Glu Thr
        35                  40                  45

Glu Ser Pro Thr Val Glu Asn Lys Gln Cys Ala Gly Lys
    50                  55                  60


<210> SEQ ID NO 15
<211> LENGTH: 487
<212> TYPE: PRT
<213> ORGANISM: Cucumis melo
<220> FEATURE:
<221> NAME/KEY: VARIANT
```

-continued

```
<222> LOCATION: (1)...(487)
<223> OTHER INFORMATION: Xaa = Any Amino Acid
<221> NAME/KEY: misc_feature
<222> LOCATION: (0)...(0)
<223> OTHER INFORMATION: Accession No. AF081955

<400> SEQUENCE: 15

Met Ala Thr Pro Ser Ser Ser Ser Pro Glu Leu Pro Leu Lys Pro Ile
 1               5                  10                  15

Pro Gly Gly Tyr Gly Phe Pro Phe Leu Gly Pro Ile Lys Asp Arg Tyr
            20                  25                  30

Asp Tyr Phe Tyr Phe Gln Gly Arg Asp Glu Phe Phe Glu Arg Ser Arg
        35                  40                  45

Ile Thr Lys Tyr Asn Ser Thr Val Phe Arg Ala Asn Met Pro Pro Gly
    50                  55                  60

Pro Phe Ile Ser Ser Asp Ser Arg Val Val Val Leu Leu Asp Ala Leu
65                  70                  75                  80

Ser Phe Pro Ile Leu Phe Asp Thr Ala Lys Val Glu Lys Arg Asn Ile
                85                  90                  95

Leu Asp Gly Thr Tyr Met Pro Ser Leu Ser Phe Thr Gly Asn Ile Arg
            100                 105                 110

Thr Cys Ala Tyr Leu Asp Pro Ser Glu Thr Glu His Ser Val Leu Lys
        115                 120                 125

Arg Leu Phe Leu Ser Phe Leu Ala Ser Arg His Asp Arg Phe Ile Pro
    130                 135                 140

Leu Phe Arg Ser Ser Leu Ser Glu Met Phe Val Lys Leu Glu Asp Lys
145                 150                 155                 160

Leu Ser Glu Lys Lys Lys Ile Ala Asp Phe Asn Ser Ile Ser Asp Ser
                165                 170                 175

Met Ser Phe Asp Tyr Val Phe Arg Leu Leu Ser Asp Gly Thr Pro Asp
            180                 185                 190

Ser Lys Leu Ala Ala Glu Gly Pro Gly Met Phe Asp Leu Trp Leu Val
        195                 200                 205

Phe Gln Leu Ala Pro Leu Ala Ser Ile Gly Leu Pro Lys Ile Phe Ser
    210                 215                 220

Val Phe Glu Asp Leu Val Ile His Thr Ile Pro Leu Pro Phe Phe Pro
225                 230                 235                 240

Val Lys Ser Gly Tyr Arg Lys Leu Tyr Glu Ala Phe Tyr Ser Ser Ser
                245                 250                 255

Gly Ser Phe Leu Asp Glu Ala Glu Lys Gln Gly Ile Asp Arg Glu Lys
            260                 265                 270

Ala Cys His Asn Leu Val Phe Leu Ala Gly Phe Asn Ala Tyr Gly Gly
        275                 280                 285

Met Lys Val Leu Phe Pro Thr Leu Leu Lys Trp Val Gly Thr Ala Gly
    290                 295                 300

Glu Asp Leu His Arg Lys Leu Ala Glu Glu Val Arg Thr Thr Val Lys
305                 310                 315                 320

Glu Glu Gly Gly Leu Thr Phe Ser Ala Leu Glu Lys Met Ser Leu Leu
                325                 330                 335

Lys Ser Val Val Tyr Glu Ala Leu Arg Ile Glu Pro Pro Val Pro Phe
            340                 345                 350

Gln Tyr Gly Lys Ala Lys Glu Asp Ile Val Ile Gln Ser His Asp Ser
        355                 360                 365

Ser Phe Lys Ile Lys Lys Gly Glu Thr Ile Phe Gly Tyr Gln Pro Phe
    370                 375                 380
```

```
Ala Thr Lys Asp Pro Lys Ile Phe Lys Asp Ser Glu Lys Phe Val Gly
385                 390                 395                 400

Asp Arg Phe Val Gly Glu Glu Gly Glu Lys Leu Leu Lys Tyr Val Tyr
                405                 410                 415

Trp Ser Asn Glu Arg Glu Thr Val Glu Pro Thr Arg Xaa Asn Lys Gln
            420                 425                 430

Cys Pro Gly Lys Asn Leu Val Val Leu Ile Gly Arg Ile Met Val Val
        435                 440                 445

Glu Phe Phe Leu Arg Tyr Asp Thr Phe Thr Val Glu Val Ala Asp Leu
    450                 455                 460

Pro Leu Gly Pro Ala Val Lys Phe Lys Ser Leu Thr Arg Ala Thr Asp
465                 470                 475                 480

Met Leu Lys Leu Met Thr Asn
                485


<210> SEQ ID NO 16
<211> LENGTH: 23
<212> TYPE: DNA
<213> ORGANISM: Artificial Sequence
<220> FEATURE:
<221> NAME/KEY: misc_feature
<222> LOCATION: (1)...(23)
<223> OTHER INFORMATION: n = A,T,C or G
      y = C or T(U)
<223> OTHER INFORMATION: Description of Artificial Sequence:/Note =
      synthetic construct

<400> SEQUENCE: 16

ggtgagttgc tntgyggnta yca                                          23


<210> SEQ ID NO 17
<211> LENGTH: 20
<212> TYPE: DNA
<213> ORGANISM: Artificial Sequence
<220> FEATURE:
<221> NAME/KEY: misc_feature
<222> LOCATION: (1)...(20)
<223> OTHER INFORMATION: n = A,T,C or G
      y = A,T,C or G
<223> OTHER INFORMATION: Description of Artificial Sequence:/Note =
      synthetic construct

<400> SEQUENCE: 17

ggtgagttgc tntgyggnta                                              20


<210> SEQ ID NO 18
<211> LENGTH: 20
<212> TYPE: DNA
<213> ORGANISM: Artificial Sequence
<220> FEATURE:
<221> NAME/KEY: misc_feature
<222> LOCATION: (1)...(20)
<223> OTHER INFORMATION: n = A,T,C or G
      y = C or T(U)
<223> OTHER INFORMATION: Description of Artificial Sequence:/Note =
      synthetic construct

<400> SEQUENCE: 18

tggtcnaayg gnccrgagac                                              20


<210> SEQ ID NO 19
<211> LENGTH: 23
<212> TYPE: DNA
<213> ORGANISM: Artificial Sequence
<220> FEATURE:
```

```
<221> NAME/KEY: misc_feature
<222> LOCATION: (1)...(23)
<223> OTHER INFORMATION: n = A,T,C or G
      y = C or T(U)
      r = A or G
<223> OTHER INFORMATION: Description of Artificial Sequence:/Note =
      synthetic construct

<400> SEQUENCE: 19

tactggtcna ayggnccnsa rac                                             23


<210> SEQ ID NO 20
<211> LENGTH: 24
<212> TYPE: DNA
<213> ORGANISM: Artificial Sequence
<220> FEATURE:
<221> NAME/KEY: misc_feature
<222> LOCATION: (1)...(24)
<223> OTHER INFORMATION: n = A,T,C or G
      y = C or T(U)
      r = A or G
<223> OTHER INFORMATION: Description of Artificial Sequence:/Note =
      synthetic construct

<400> SEQUENCE: 20

aayaarcart gygcngctaa ggac                                            24


<210> SEQ ID NO 21
<211> LENGTH: 21
<212> TYPE: DNA
<213> ORGANISM: Artificial Sequence
<220> FEATURE:
<221> NAME/KEY: misc_feature
<222> LOCATION: (1)...(21)
<223> OTHER INFORMATION: n = A,T,C or G
      y = C or T(U)
      r = A or G
<223> OTHER INFORMATION: Description of Artificial Sequence:/Note =
      synthetic construct

<400> SEQUENCE: 21

aarcartgyg cngctaagga c                                               21


<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 22

Gly Glu Leu Leu Cys Gly Tyr Gln
 1               5


<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 23

Gly Glu Leu Leu Cys Gly Tyr
 1               5


<210> SEQ ID NO 24
<211> LENGTH: 7
```

```
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 24

Trp Ser Asn Gly Pro Glu Thr
 1               5


<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 25

Tyr Trp Ser Asn Gly Pro Glu Thr
 1               5


<210> SEQ ID NO 26
<211> LENGTH: 8
<212> TYPE: PRT
<213> ORGANISM: Artificial Sequence
<220> FEATURE:
<221> NAME/KEY: VARIANT
<222> LOCATION: (1)...(8)
<223> OTHER INFORMATION: Xaa = Any Amino Acid
<223> OTHER INFORMATION: Description of Artificial Sequence:/Note =
      synthetic construct

<400> SEQUENCE: 26

Asn Lys Gln Cys Ala Ala Xaa Xaa
 1               5


<210> SEQ ID NO 27
<211> LENGTH: 7
<212> TYPE: PRT
<213> ORGANISM: Artificial Sequence
<220> FEATURE:
<221> NAME/KEY: VARIANT
<222> LOCATION: (1)...(7)
<223> OTHER INFORMATION: Xaa = Any Amino Acid
<223> OTHER INFORMATION: Description of Artificial Sequence:/Note =
      synthetic construct

<400> SEQUENCE: 27

Lys Gln Cys Ala Ala Xaa Xaa
 1               5


<210> SEQ ID NO 28
<211> LENGTH: 32
<212> TYPE: PRT
<213> ORGANISM: Cucumis melo

<400> SEQUENCE: 28

Gly Glu Leu Leu Cys Gly Tyr Gln Pro Leu Val Met Arg Asp Pro Lys
 1               5                  10                  15

Val Phe Asp Glu Pro Glu Ala Phe Asn Pro Asp Arg Phe Arg Gly Glu
            20                  25                  30


<210> SEQ ID NO 29
<211> LENGTH: 32
<212> TYPE: PRT
<213> ORGANISM: Cucumis melo
```

<400> SEQUENCE: 29

```
Gly Glu Leu Leu Cys Gly Tyr Gln Pro Phe Ala Thr Arg Asp Pro Lys
 1              5                   10                  15

Ile Phe Asp Arg Ala Asp Glu Phe Val Pro Asp Arg Phe Thr Gly Glu
            20                  25                  30
```

<210> SEQ ID NO 30
<211> LENGTH: 32
<212> TYPE: PRT
<213> ORGANISM: Cucumis melo

<400> SEQUENCE: 30

```
Gly Glu Leu Leu Cys Gly Tyr Gln Pro Phe Ala Thr Lys Asp Pro Lys
 1              5                   10                  15

Ile Phe Lys Asp Ser Glu Lys Phe Val Gly Asp Arg Phe Val Gly Glu
            20                  25                  30
```

<210> SEQ ID NO 31
<211> LENGTH: 272
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 31

```
agctaatgac taattagttt tatcatttac agatagtgaa ttggttgatg cacggaagct     60

gtggcggact gcgcacacat gattgagtac ttggggttat taaagtaatt tcgttgtgat    120

ccacgtggtc ttattttaat ttgagatctc attgtgtgtt gtaacccacc ggtcatctta    180

ttttatagtt tgtttgtttt ctcaattatg ctccaaattt taaaataaat aaataccatc    240

ttcttctttt tactaaaaaa aaaaaaaaaa aa                                  272
```

<210> SEQ ID NO 32
<211> LENGTH: 480
<212> TYPE: PRT
<213> ORGANISM: Capsicum annum (green pepper)

<400> SEQUENCE: 32

```
Met Ile Pro Ile Met Ser Ser Ala Pro Leu Ser Thr Ala Thr Pro Ile
 1              5                   10                  15

Ser Leu Pro Val Arg Lys Ile Pro Gly Ser Tyr Gly Phe Pro Leu Leu
            20                  25                  30

Gly Pro Leu Trp Asp Arg Leu Asp Tyr Asn Trp Phe Gln Lys Leu Pro
        35                  40                  45

Asp Phe Phe Ser Lys Arg Val Glu Lys Tyr Asn Ser Thr Val Phe Arg
    50                  55                  60

Thr Asn Val Pro Pro Cys Phe Pro Phe Phe Leu Gly Val Asn Pro Asn
65                  70                  75                  80

Val Val Ala Val Leu Asp Val Lys Ser Phe Ala His Leu Phe Asp Met
                85                  90                  95

Glu Ile Val Glu Lys Ala Asn Val Leu Val Gly Asp Phe Met Pro Ser
            100                 105                 110

Val Val Tyr Thr Gly Asp Met Arg Val Cys Ala Tyr Leu Asp Thr Ser
        115                 120                 125

Glu Pro Lys His Thr Gln Ile Lys Asn Phe Ser Leu Asp Ile Leu Lys
    130                 135                 140

Arg Ser Ser Lys Thr Trp Val Pro Thr Leu Val Lys Glu Leu Asp Thr
```

-continued

```
145                 150                 155                 160

Leu Phe Gly Thr Phe Glu Ser Asp Leu Ser Lys Ser Lys Ser Ala Ser
                165                 170                 175

Leu Leu Pro Ala Leu Gln Lys Phe Leu Phe Asn Phe Phe Ser Leu Thr
            180                 185                 190

Phe Leu Gly Ala Asp Pro Ser Ala Ser Pro Glu Ile Ala Asn Ser Gly
        195                 200                 205

Phe Ala Tyr Leu Asp Ala Trp Leu Ala Ile Gln Leu Ala Pro Thr Val
    210                 215                 220

Ser Ile Gly Val Leu Gln Pro Leu Glu Glu Ile Phe Val His Ser Phe
225                 230                 235                 240

Ser Tyr Pro Tyr Phe Leu Val Arg Gly Gly Tyr Glu Lys Leu Ile Lys
                245                 250                 255

Phe Val Lys Ser Glu Ala Lys Glu Val Leu Thr Arg Ala Gln Thr Asp
            260                 265                 270

Phe Gln Leu Thr Glu Gln Glu Ala Ile His Asn Leu Leu Phe Ile Leu
        275                 280                 285

Gly Phe Asn Ala Phe Gly Gly Phe Thr Ile Phe Leu Pro Thr Leu Leu
    290                 295                 300

Gly Asn Leu Gly Asp Glu Lys Asn Ala Glu Met Gln Glu Lys Leu Arg
305                 310                 315                 320

Lys Glu Val Arg Glu Lys Val Gly Thr Asn Gln Glu Asn Leu Ser Phe
                325                 330                 335

Glu Ser Val Lys Glu Met Glu Leu Val Gln Ser Phe Val Tyr Glu Ser
            340                 345                 350

Leu Arg Leu Ser Pro Pro Val Pro Ser Gln Tyr Ala Arg Ala Arg Lys
        355                 360                 365

Asp Phe Met Leu Ser Ser His Asp Ser Val Tyr Glu Ile Lys Lys Gly
    370                 375                 380

Glu Leu Leu Cys Gly Tyr Gln Pro Leu Val Met Lys Asp Pro Lys Val
385                 390                 395                 400

Phe Asp Glu Pro Glu Lys Phe Met Leu Glu Arg Phe Thr Lys Glu Lys
                405                 410                 415

Gly Lys Glu Leu Leu Asn Tyr Leu Phe Trp Ser Asn Gly Pro Gln Thr
            420                 425                 430

Gly Ser Pro Thr Glu Ser Asn Lys Gln Cys Ala Ala Lys Asp Ala Val
        435                 440                 445

Thr Leu Thr Ala Ser Leu Ile Val Ala Tyr Ile Phe Gln Lys Tyr Asp
    450                 455                 460

Ser Val Ser Phe Ser Ser Gly Ser Leu Thr Ser Val Lys Lys Ala Cys
465                 470                 475                 480
```

<210> SEQ ID NO 33
<211> LENGTH: 483
<212> TYPE: PRT
<213> ORGANISM: Banana

<400> SEQUENCE: 33

```
Met Ala Met Met Trp Ser Ser Ala Ser Ala Thr Ala Val Thr Thr Leu
 1               5                  10                  15

Pro Thr Arg Pro Ile Pro Gly Ser Tyr Gly Pro Pro Leu Val Gly Pro
            20                  25                  30

Leu Lys Asp Arg Leu Asp Tyr Phe Trp Phe Gln Gly Pro Glu Thr Phe
        35                  40                  45
```

-continued

```
Phe Arg Ser Arg Met Ala Thr His Lys Ser Thr Val Phe Arg Thr Asn
    50                  55                  60

Met Pro Pro Thr Phe Pro Phe Phe Val Gly Val Asp Pro Arg Val Val
65                  70                  75                  80

Thr Val Leu Asp Cys Thr Ser Phe Ser Ala Leu Phe Asp Leu Glu Val
                85                  90                  95

Val Glu Lys Lys Asn Ile Leu Ile Gly Asp Tyr Met Pro Ser Leu Ser
            100                 105                 110

Phe Thr Gly Asp Thr Arg Val Val Val Tyr Leu Asp Pro Ser Glu Pro
        115                 120                 125

Asp His Ala Arg Val Lys Ser Phe Cys Leu Glu Leu Leu Arg Arg Gly
    130                 135                 140

Ala Lys Thr Trp Val Ser Ser Phe Leu Ser Asn Leu Asp Val Met Leu
145                 150                 155                 160

Ala Thr Ile Glu Gln Gly Ile Ala Lys Asp Gly Ser Ala Gly Leu Phe
                165                 170                 175

Gly Pro Leu Gln Lys Cys Ile Phe Ala Phe Leu Cys Lys Ser Ile Ile
            180                 185                 190

Gly Ala Asp Pro Ser Val Ser Pro Asp Val Gly Glu Asn Gly Phe Val
        195                 200                 205

Met Leu Asp Lys Trp Leu Ala Leu Gln Leu Leu Pro Thr Val Lys Val
    210                 215                 220

Gly Ala Ile Pro Gln Pro Leu Glu Glu Ile Leu Leu His Ser Phe Pro
225                 230                 235                 240

Leu Pro Phe Phe Leu Val Ser Arg Asp Tyr Arg Lys Leu Tyr Glu Phe
                245                 250                 255

Val Glu Lys Gln Gly Gln Glu Val Val Arg Arg Ala Glu Thr Glu His
            260                 265                 270

Gly Leu Ser Lys His Asp Ala Ile Asn Asn Ile Leu Phe Val Leu Gly
        275                 280                 285

Phe Asn Ala Phe Gly Gly Phe Ser Val Phe Phe Pro Thr Leu Leu Thr
    290                 295                 300

Thr Ile Gly Arg Asp Lys Thr Gly Leu Arg Glu Lys Leu Lys Asp Glu
305                 310                 315                 320

Val Arg Arg Val Met Lys Ser Arg Gly Glu Lys Arg Pro Ser Phe Glu
                325                 330                 335

Thr Val Arg Glu Met Glu Leu Val Arg Ser Thr Val Tyr Glu Val Leu
            340                 345                 350

Arg Leu Asn Pro Pro Val Pro Leu Gln Tyr Gly Arg Ala Arg Thr Asp
        355                 360                 365

Phe Thr Leu Asn Ser His Asp Ala Ala Phe Lys Val Glu Lys Gly Glu
    370                 375                 380

Leu Leu Cys Gly Tyr Gln Pro Leu Val Met Arg Asp Pro Ala Val Phe
385                 390                 395                 400

Asp Asp Pro Glu Thr Phe Ala Pro Glu Arg Phe Met Gly Ser Gly Lys
                405                 410                 415

Glu Leu Leu Lys Tyr Val Phe Trp Ser Asn Gly Pro Glu Thr Gly Thr
            420                 425                 430

Pro Thr Pro Ala Asn Lys Gln Cys Ala Ala Lys Asp Tyr Val Val Glu
        435                 440                 445

Thr Ala Cys Leu Leu Met Ala Glu Ile Phe Tyr Arg Tyr Asp Glu Phe
    450                 455                 460

Val Cys Ala Asp Asp Ala Ile Ser Val Thr Lys Leu Asp Arg Ala Arg
```

-continued

```
465                 470                 475                 480

Glu Trp Glu


<210> SEQ ID NO 34
<211> LENGTH: 21
<212> TYPE: DNA
<213> ORGANISM: Artificial Sequence
<220> FEATURE: 745:>220>
<223> OTHER INFORMATION: Description of Artificial Sequence:/Note =
      synthetic construct

<400> SEQUENCE: 34

ggttatcagc cgctggtgat g                                                21


<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 35

atgaaccgga ggcgtttaat ccg                                              23


<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 36

acagagcgga cgagttcgta cct                                              23


<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 37

aggattcgga gaagttcgtg ggc                                              23


<210> SEQ ID NO 38
<211> LENGTH: 488
<212> TYPE: PRT
<213> ORGANISM: Psidium guava

<400> SEQUENCE: 38

Met Ala Arg Val Val Met Ser Asn Met Ser Pro Ala Met Ser Ser Thr
 1               5                  10                  15

Tyr Pro Pro Ser Leu Ser Pro Pro Ser Ser Pro Arg Pro Thr Thr Leu
            20                  25                  30

Pro Val Arg Thr Ile Pro Gly Ser Tyr Gly Trp Pro Leu Leu Gly Pro
        35                  40                  45

Ile Ser Asp Arg Leu Asp Tyr Phe Trp Phe Gln Gly Pro Glu Thr Phe
    50                  55                  60

Phe Arg Lys Arg Ile Glu Lys Tyr Lys Ser Thr Val Phe Arg Ala Asn
65                  70                  75                  80
```

-continued

```
Val Pro Pro Cys Phe Pro Phe Phe Ser Asn Val Asn Pro Asn Val Val
                85                  90                  95

Val Val Leu Asp Cys Glu Ser Phe Ala His Leu Phe Asp Met Glu Ile
            100                 105                 110

Val Glu Lys Ser Asn Val Leu Val Gly Asp Phe Met Pro Ser Val Lys
        115                 120                 125

Tyr Thr Gly Asn Ile Arg Val Cys Ala Tyr Leu Asp Thr Ser Glu Pro
    130                 135                 140

Gln His Ala Gln Val Lys Asn Phe Ala Met Asp Ile Leu Lys Arg Ser
145                 150                 155                 160

Ser Lys Val Trp Glu Ser Glu Val Ile Ser Asn Leu Asp Thr Met Trp
                165                 170                 175

Asp Thr Ile Glu Ser Ser Leu Ala Lys Asp Gly Asn Ala Ser Val Ile
            180                 185                 190

Phe Pro Leu Gln Lys Phe Leu Phe Asn Phe Leu Ser Lys Ser Ile Ile
        195                 200                 205

Gly Ala Asp Pro Ala Ala Ser Pro Gln Val Ala Lys Ser Gly Tyr Ala
    210                 215                 220

Met Leu Asp Arg Trp Leu Ala Leu Gln Leu Leu Pro Thr Ile Asn Ile
225                 230                 235                 240

Gly Val Leu Gln Pro Leu Val Glu Ile Phe Leu His Ser Trp Ala Tyr
                245                 250                 255

Pro Phe Ala Leu Val Ser Gly Asp Tyr Asn Lys Leu Tyr Gln Phe Ile
            260                 265                 270

Glu Lys Glu Gly Arg Glu Ala Val Glu Arg Ala Lys Ala Glu Phe Gly
        275                 280                 285

Leu Thr His Gln Glu Ala Ile His Asn Leu Leu Phe Ile Leu Gly Phe
    290                 295                 300

Asn Ala Phe Gly Gly Phe Ser Ile Phe Leu Pro Thr Leu Leu Ser Asn
305                 310                 315                 320

Ile Leu Ser Asp Thr Thr Gly Leu Gln Asp Arg Leu Arg Lys Glu Val
                325                 330                 335

Arg Ala Lys Gly Gly Pro Ala Leu Ser Phe Ala Ser Val Lys Glu Met
            340                 345                 350

Glu Leu Val Lys Ser Val Val Tyr Glu Thr Leu Arg Leu Asn Pro Pro
        355                 360                 365

Val Pro Phe Gln Tyr Ala Arg Ala Arg Lys Asp Phe Gln Leu Lys Ser
    370                 375                 380

His Asp Ser Val Phe Asp Val Lys Lys Gly Glu Leu Leu Cys Gly Tyr
385                 390                 395                 400

Gln Lys Val Val Met Thr Asp Pro Lys Val Phe Asp Glu Pro Glu Ser
                405                 410                 415

Phe Asn Ser Asp Arg Phe Val Gln Asn Ser Glu Leu Leu Asp Tyr Leu
            420                 425                 430

Tyr Trp Ser Asn Gly Pro Gln Thr Gly Thr Pro Thr Glu Ser Asn Lys
        435                 440                 445

Gln Cys Ala Ala Lys Asp Tyr Val Thr Leu Thr Ala Cys Leu Phe Val
    450                 455                 460

Ala Tyr Met Phe Arg Arg Tyr Asn Ser Val Thr Gly Ser Ser Ser Ser
465                 470                 475                 480

Ile Thr Ala Val Glu Lys Ala Asn
                485
```

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 39
ccgtcagcac caccaaatcc ttc 23

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 40
gaacagataa tccagcaggg c 21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 41
ctgaaccgac cgcgactgtg t 21

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 42
tcgcccgtga accgatcagg ta 22

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 43
tccgcgtcgg ctccactgtc 20

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 44
tctcccacga acctatcgcc ca 22

<210> SEQ ID NO 45

<211> LENGTH: 26
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 45
gccatggcct ccattgtcat tccttc 26

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 46
ggaattctta gtgatggtga tggtgatgga aacttgcttt cttag 45

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 47
gcatatggct actccttctt cctcctc 27

<210> SEQ ID NO 48
<211> LENGTH: 46
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 48
catcgattta gtgatggtga tggtgatgat tagtcattag ctttaa 46

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 49
atgaattcgg tacccgggat cctttttttt ttttttttt 39

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 50
atgaattcgg tacccgggat c 21

<210> SEQ ID NO 51
<211> LENGTH: 1596

-continued

<212> TYPE: DNA
<213> ORGANISM: Cucumis melo

<400> SEQUENCE: 51

```
atgtcctcca ttgtcattcc ttctcttcaa cctcacttgc gattcccatc ctcgcaagaa     60
acgcctcaaa gatctcgttc tagagttggc ttcgtttcca tacgtccaat ctacgccacc    120
gacggagttt cttcctcgtc ttcttcctct cttcaagtgc cgcagcggat tgtttcgccg    180
ccggaaccca ccaagcttcc tttgaggaag gttcccggtg attatgggcc accgatgttt    240
ggggcgttga aggacagaca tgattatttt tataatcagg ggagggaaga gtatttgaaa    300
tctcgaatgc tccggtatga atccactgtg tatagaacta atatgccgcc gggtccattt    360
atcacttccg attcccgagt tgttgtttta ctcgacggga agagttttcc tgttcttttc    420
gaccattcta aagttgagaa gaaagatctc tttatcggaa cttacatgcc tgtaacagag    480
ctcaccggcg gttacagggt gctttcttat attgacccat ctgagcccga tcacgctaag    540
cttaaacagt tgattttctt tctcctcaag caccgccggg ataaaattat gccggaattt    600
cactctactt tttctgagct attcgagact ctggaaaagg atttggctgc tgctggtaga    660
gcagagtaca atgcttccgg tgaacaagcg gcgtttaatt tcttggctcg gtctcttttc    720
ggcgctgatc cggtagattc caaattgggt cgcgatgcgc cgaaattgat cgcgaaatgg    780
gtcttattcc agcttggccc tgttctgagt ctcggcctcc ccaaggtcgt cgaggagctt    840
ctcctccgca cggtccggct ccccccggcg ttgattaaag ccgattaccg tcggttgtac    900
gacttctttt acaagtcgtc ggaggcggtg tttgaggagg cggatagatt gggaatttcg    960
agggaagaag cttgtcacaa cttgctattc acaacttgtt ttaattcatt tggagggatg   1020
aagatctttt tccccaatat gataaaatgg atcggccgag ccggagtgaa tctccacacc   1080
cgactagcac gggagattcg tactgccgta aaagccaacg gcgggaaaat cacgatgggg   1140
gctatggaac agatgccgct gatgaaatca gtggtgtacg aagcgttaag aatcgagccg   1200
ccggttccgg ttcagtacgg tcgggcaaag aaagaccttg tggtggaaag ccacgacgcg   1260
gctttcgaga tcaaagaagg agaagtgatt tgtgggtatc agccattcgc aacaagagat   1320
ccgaaaatct tcgacagagc ggacgagttc gtacctgatc ggttcacggg cgagggtgag   1380
gagcttctca aacacgtcat atggtcaaac ggaccggaaa cacagtcgcc gtcggttcag   1440
aacaagcagt gcgcaggaaa agacttcatc gtcttcatct ctcggcttct cgtcgttgaa   1500
cttttcctcc gttacgactc cttcgacatc gaagcctcaa acactccgtt aggtgccgcc   1560
gtcaccgtaa cctccctaaa gaaagcaagt ttctaa                             1596
```

<210> SEQ ID NO 52
<211> LENGTH: 465
<212> TYPE: PRT
<213> ORGANISM: Cucumis melo

<400> SEQUENCE: 52

```
Asn Asp Met Ser Ser Ile Val Ile Pro Ser Leu Gln Pro His Leu Arg
 1               5                  10                  15

Phe Pro Ser Ser Gln Glu Thr Pro Gln Arg Ser Arg Ser Arg Val Gly
            20                  25                  30

Phe Val Ser Ile Arg Pro Ile Tyr Ala Thr Asp Gly Val Ser Ser Ser
        35                  40                  45

Ser Ser Ser Ser Leu Gln Val Pro Gln Arg Ile Val Ser Pro Pro Glu
    50                  55                  60
```

-continued

```
Pro Thr Lys Leu Pro Leu Arg Lys Val Pro Gly Asp Tyr Gly Pro Pro
65                  70                  75                  80

Met Phe Gly Ala Leu Lys Asp Arg His Asp Tyr Phe Tyr Asn Gln Gly
                85                  90                  95

Arg Glu Glu Tyr Leu Lys Ser Arg Met Leu Arg Tyr Glu Ser Thr Val
            100                 105                 110

Tyr Arg Thr Asn Met Pro Pro Gly Pro Phe Ile Thr Ser Asp Ser Arg
        115                 120                 125

Val Val Val Leu Leu Asp Gly Lys Ser Phe Pro Val Leu Phe Asp His
    130                 135                 140

Ser Lys Val Glu Lys Lys Asp Leu Phe Thr Gly Ala Val Phe Glu Glu
145                 150                 155                 160

Ala Asp Arg Leu Gly Ile Ser Arg Glu Glu Ala Cys His Asn Leu Leu
                165                 170                 175

Phe Thr Thr Cys Phe Asn Ser Phe Gly Gly Met Lys Ile Phe Phe Pro
            180                 185                 190

Asn Met Ile Lys Trp Ile Gly Arg Ala Gly Val Asn Leu His Thr Arg
        195                 200                 205

Leu Ala Arg Glu Ile Arg Thr Ala Val Lys Ala Asn Gly Gly Lys Ile
    210                 215                 220

Thr Met Gly Ala Met Glu Gln Met Pro Leu Met Lys Ser Val Val Tyr
225                 230                 235                 240

Glu Ala Leu Arg Ile Glu Pro Pro Val Pro Val Gln Tyr Gly Arg Ala
                245                 250                 255

Lys Lys Asp Leu Val Val Glu Ser His Asp Ala Ala Phe Glu Ile Lys
            260                 265                 270

Glu Gly Glu Val Ile Cys Gly Tyr Gln Pro Phe Ala Thr Arg Asp Pro
        275                 280                 285

Lys Ile Phe Asp Arg Ala Asp Glu Leu Val Pro Asp Arg Phe Thr Gly
    290                 295                 300

Glu Gly Glu Glu Leu Leu Thr Tyr Met Pro Val Thr Glu Leu Thr Gly
305                 310                 315                 320

Gly Tyr Arg Val Leu Ser Tyr Ile Asp Pro Ser Glu Pro Asp His Ala
                325                 330                 335

Lys Leu Lys Gln Leu Ile Phe Phe Leu Leu Lys His Arg Arg Asp Lys
            340                 345                 350

Ile Met Pro Glu Phe His Ser Thr Phe Ser Glu Leu Phe Glu Thr Leu
        355                 360                 365

Glu Lys Asp Leu Ala Ala Ala Gly Arg Ala Glu Tyr Asn Ala Ser Gly
    370                 375                 380

Glu Gln Ala Ala Phe Asn Phe Leu Ala Arg Ser Leu Phe Gly Ala Asp
385                 390                 395                 400

Pro Val Asp Ser Lys Leu Gly Arg Asp Ala Pro Lys Leu Ile Ala Lys
                405                 410                 415

Trp Val Leu Phe Gln Leu Gly Pro Val Leu Ser Leu Gly Leu Pro Lys
            420                 425                 430

Val Val Glu Glu Leu Leu Leu Arg Thr Val Arg Leu Pro Pro Ala Leu
        435                 440                 445

Ile Lys Ala Asp Tyr Arg Arg Leu Tyr Asp Phe Phe Tyr Lys Ser Ser
    450                 455                 460

Glu
465
```

-continued

<210> SEQ ID NO 53
<211> LENGTH: 468
<212> TYPE: PRT
<213> ORGANISM: Flax

<400> SEQUENCE: 53

```
Met Ala Ser Ser Ala Leu Asn Asn Leu Val Ala Val Asn Pro Asn Thr
 1               5                  10                  15

Leu Ser Pro Ser Pro Lys Ser Thr Pro Leu Pro Asn Thr Phe Ser Asn
            20                  25                  30

Leu Arg Arg Val Ser Ala Phe Arg Pro Ile Lys Ala Ser Leu Phe Gly
        35                  40                  45

Asp Ser Pro Ile Lys Ile Pro Gly Ile Thr Ser Gln Pro Pro Pro Ser
    50                  55                  60

Ser Asp Glu Thr Thr Leu Pro Ile Arg Gln Ile Pro Gly Asp Tyr Gly
65                  70                  75                  80

Leu Pro Gly Ile Gly Pro Ile Gln Asp Arg Leu Asp Tyr Phe Tyr Asn
                85                  90                  95

Gln Gly Arg Glu Glu Phe Phe Lys Ser Arg Leu Gln Lys Tyr Lys Ser
            100                 105                 110

Thr Val Tyr Arg Ala Asn Met Pro Pro Gly Pro Phe Ile Ala Ser Asn
        115                 120                 125

Pro Arg Val Ile Val Leu Leu Asp Ala Lys Ser Phe Pro Val Leu Phe
    130                 135                 140

Asp Met Ser Lys Val Glu Lys Lys Asp Leu Phe Thr Gly Ser Val Leu
145                 150                 155                 160

Asp Glu Ala Glu Gln Ser Gly Ile Ser Arg Asp Glu Ala Cys His Asn
                165                 170                 175

Ile Leu Phe Ala Val Cys Phe Asn Ser Trp Gly Gly Phe Lys Ile Leu
            180                 185                 190

Phe Pro Ser Leu Met Lys Trp Ile Gly Arg Ala Gly Leu Glu Leu His
        195                 200                 205

Thr Lys Leu Ala Gln Glu Ile Arg Ser Ala Ile Gln Ser Thr Gly Gly
    210                 215                 220

Gly Lys Val Thr Met Ala Ala Met Glu Gln Met Pro Leu Met Lys Ser
225                 230                 235                 240

Val Val Tyr Glu Thr Leu Arg Ile Glu Pro Pro Val Ala Leu Gln Tyr
                245                 250                 255

Gly Lys Ala Lys Lys Asp Phe Ile Leu Glu Ser His Glu Ala Ala Tyr
            260                 265                 270

Gln Val Lys Glu Gly Glu Met Leu Phe Gly Tyr Gln Pro Phe Ala Thr
        275                 280                 285

Lys Asp Pro Lys Ile Phe Asp Arg Pro Glu Glu Phe Val Ala Asp Arg
    290                 295                 300

Phe Val Gly Glu Gly Val Lys Leu Met Thr Tyr Met Pro Ser Thr Glu
305                 310                 315                 320

Leu Thr Gly Gly Tyr Arg Ile Leu Ser Tyr Leu Asp Pro Ser Glu Pro
                325                 330                 335

Asn His Thr Lys Leu Lys Gln Leu Leu Phe Asn Leu Ile Lys Asn Arg
            340                 345                 350

Arg Asp Tyr Val Ile Pro Glu Phe Ser Ser Ser Phe Thr Asp Leu Cys
        355                 360                 365

Glu Val Val Glu Tyr Asp Leu Ala Thr Lys Gly Lys Ala Ala Phe Asn
    370                 375                 380
```

-continued

```
Asp Pro Ala Glu Gln Ala Ala Phe Asn Phe Leu Ser Arg Ala Phe Phe
385                 390                 395                 400

Gly Val Lys Pro Ile Asp Thr Pro Leu Gly Lys Asp Ala Pro Ser Leu
                405                 410                 415

Ile Ser Lys Trp Val Leu Phe Asn Leu Ala Pro Ile Leu Ser Val Gly
            420                 425                 430

Leu Pro Lys Glu Val Glu Glu Ala Thr Leu His Ser Val Arg Leu Pro
        435                 440                 445

Pro Leu Leu Val Gln Asn Asp Tyr His Arg Leu Tyr Glu Phe Phe Thr
    450                 455                 460

Ser Ala Ala Gly
465


<210> SEQ ID NO 54
<211> LENGTH: 405
<212> TYPE: PRT
<213> ORGANISM: Guayule

<400> SEQUENCE: 54

Met Asp Pro Ser Ser Lys Pro Leu Arg Glu Ile Pro Gly Ser Tyr Gly
 1               5                  10                  15

Ile Pro Phe Phe Gln Pro Ile Lys Asp Arg Leu Glu Tyr Phe Tyr Gly
            20                  25                  30

Thr Gly Gly Arg Asp Glu Tyr Phe Arg Ser Arg Met Gln Lys Tyr Gln
        35                  40                  45

Ser Thr Val Phe Arg Ala Asn Met Pro Pro Gly Pro Phe Val Ser Ser
    50                  55                  60

Asn Pro Lys Val Ile Val Leu Leu Asp Ala Lys Ser Phe Pro Ile Leu
65                  70                  75                  80

Phe Asp Val Ser Lys Val Glu Lys Lys Asp Leu Phe Thr Gly Pro Val
                85                  90                  95

Met Glu Gln Ala Glu Lys Leu Gly Val Pro Lys Asp Glu Ala Val His
            100                 105                 110

Asn Ile Leu Phe Ala Val Cys Phe Asn Thr Phe Gly Gly Val Lys Ile
        115                 120                 125

Leu Phe Pro Asn Thr Leu Lys Trp Ile Gly Val Ala Gly Glu Asn Leu
    130                 135                 140

His Thr Gln Leu Ala Glu Glu Ile Arg Gly Ala Ile Lys Ser Tyr Gly
145                 150                 155                 160

Asp Gly Asn Val Thr Leu Glu Ala Ile Glu Gln Met Pro Leu Thr Lys
                165                 170                 175

Ser Val Val Tyr Glu Ser Leu Arg Ile Glu Pro Pro Val Pro Pro Gln
            180                 185                 190

Tyr Gly Lys Ala Lys Ser Asn Phe Thr Ile Glu Ser His Asp Ala Thr
        195                 200                 205

Phe Glu Val Lys Lys Gly Glu Met Leu Phe Gly Tyr Gln Pro Phe Ala
    210                 215                 220

Thr Lys Asp Pro Lys Val Phe Asp Arg Pro Glu Glu Phe Val Pro Asp
225                 230                 235                 240

Arg Phe Val Gly Asp Gly Glu Ala Leu Leu Thr Tyr Met Pro Ser Thr
                245                 250                 255

Lys Leu Thr Gly Ala Tyr Arg Val Leu Ser Tyr Leu Asp Pro Ser Glu
            260                 265                 270

Pro Arg His Ala Gln Leu Lys Asn Leu Leu Phe Phe Met Leu Lys Asn
        275                 280                 285
```

Ser Ser Asn Arg Val Ile Pro Gln Phe Glu Thr Thr Tyr Thr Glu Leu
    290                 295                 300

Phe Glu Gly Leu Glu Ala Glu Leu Ala Lys Asn Gly Lys Ala Ala Phe
305                 310                 315                 320

Asn Asp Val Gly Glu Gln Ala Ala Phe Arg Phe Leu Gly Arg Ala Tyr
                325                 330                 335

Phe Asn Ser Asn Pro Glu Glu Thr Lys Leu Gly Thr Ser Ala Pro Thr
            340                 345                 350

Leu Ile Ser Ser Trp Val Leu Phe Asn Leu Ala Pro Thr Leu Asp Leu
        355                 360                 365

Gly Leu Pro Trp Phe Leu Gln Glu Pro Leu Leu His Thr Phe Arg Leu
    370                 375                 380

Pro Ala Phe Leu Ile Lys Ser Thr Tyr Asn Lys Leu Tyr Asp Tyr Phe
385                 390                 395                 400

Gln Ser Val Ala Thr
                405

<210> SEQ ID NO 55
<211> LENGTH: 448
<212> TYPE: PRT
<213> ORGANISM: Arabidopsis

<400> SEQUENCE: 55

Met Ala Ser Ile Ser Thr Pro Phe Pro Ile Ser Leu His Pro Lys Thr
 1               5                  10                  15

Val Arg Ser Lys Pro Leu Lys Phe Arg Val Leu Thr Arg Pro Ile Lys
            20                  25                  30

Ala Ser Gly Ser Glu Thr Pro Asp Leu Thr Val Ala Thr Arg Thr Gly
        35                  40                  45

Ser Lys Asp Leu Pro Ile Arg Asn Ile Pro Gly Asn Tyr Gly Leu Pro
    50                  55                  60

Ile Val Gly Pro Ile Lys Asp Arg Trp Asp Tyr Phe Tyr Asp Gln Gly
65                  70                  75                  80

Ala Glu Glu Phe Phe Lys Ser Arg Ile Arg Lys Tyr Asn Ser Thr Val
                85                  90                  95

Tyr Arg Val Asn Met Pro Pro Gly Ala Phe Ile Ala Glu Asn Pro Gln
            100                 105                 110

Val Val Ala Leu Leu Asp Gly Lys Ser Phe Pro Val Leu Phe Asp Val
        115                 120                 125

Asp Lys Val Glu Lys Lys Asp Leu Phe Thr Gly Glu Ile Leu Val Glu
    130                 135                 140

Ala Asp Lys Leu Gly Ile Ser Arg Glu Glu Ala Thr His Asn Leu Leu
145                 150                 155                 160

Phe Ala Thr Ser Phe Asn Thr Trp Gly Gly Met Lys Ile Leu Phe Pro
                165                 170                 175

Asn Met Val Lys Arg Ile Gly Pro Gly Gly His Gln Val His Asn Arg
            180                 185                 190

Leu Ala Glu Glu Ile Arg Ser Val Ile Lys Ser Asn Gly Gly Glu Leu
        195                 200                 205

Thr Met Gly Ala Ile Glu Lys Met Glu Leu Thr Lys Ser Val Val Tyr
    210                 215                 220

Glu Cys Leu Arg Phe Glu Pro Pro Val Thr Ala Gln Tyr Gly Arg Ala
225                 230                 235                 240

Lys Lys Asp Leu Val Ile Glu Ser His Asp Ala Ala Phe Lys Val Lys

-continued

```
            245                 250                 255

Ala Gly Glu Met Leu Tyr Gly Tyr Gln Pro Leu Ala Thr Arg Asp Pro
        260                 265                 270

Lys Ile Phe Asp Arg Ala Asp Glu Phe Val Pro Glu Arg Phe Val Gly
    275                 280                 285

Glu Glu Gly Glu Lys Leu Leu Thr Tyr Met Pro Ser Thr Glu Leu Thr
    290                 295                 300

Gly Gly Tyr Arg Ile Leu Ser Tyr Leu Asp Pro Ser Glu Pro Lys His
305                 310                 315                 320

Glu Lys Leu Lys Asn Leu Leu Phe Phe Leu Leu Lys Ser Ser Asn Arg
                325                 330                 335

Ile Phe Pro Glu Phe Gln Ala Thr Tyr Ser Glu Leu Phe Asp Ser Leu
            340                 345                 350

Glu Lys Glu Ala Phe Pro Leu Arg Glu Ser Gly Phe Arg Arg Phe Gln
        355                 360                 365

Arg Arg Asn Arg Leu Leu Phe Leu Gly Ser Ser Phe Leu Arg Asp Glu
    370                 375                 380

Ser Arg Arg Tyr Lys Leu Lys Ala Asp Ala Pro Gly Leu Ile Thr Lys
385                 390                 395                 400

Trp Val Leu Phe Asn Leu His Pro Leu Leu Ser Ile Gly Leu Pro Arg
                405                 410                 415

Val Ile Glu Glu Pro Leu Ile His Thr Phe Ser Leu Pro Pro Ala Leu
            420                 425                 430

Val Lys Ser Asp Tyr Gln Arg Leu Tyr Glu Phe Leu Arg Ile Arg Gly
        435                 440                 445
```

<210> SEQ ID NO 56
<211> LENGTH: 1715
<212> TYPE: DNA
<213> ORGANISM: Cucumis melo
<220> FEATURE:
<221> NAME/KEY: misc_feature
<222> LOCATION: 1283
<223> OTHER INFORMATION: n = A,T,C or G

<400> SEQUENCE: 56

```
atggctactc cttcttcctc ctcccctgaa cttcctctca aaccaattcc cggtggctat      60

ggcttcccct tcctcggtcc catcaaagac cgttacgatt acttctattt ccaaggtaga     120

gacgaattct tccgttcccg gattaccaaa tacaactcca ccgtcttccg cgccaacatg     180

ccaccgggcc ccttcatttc ctccgattcc agagtcgttg tccttctcga tgccctcagt     240

tttcctatcc tcttcgacac agccaaagtc gagaaacgca acattctcga cggaacttac     300

atgccctcct tgtccttcac cggcaacatt cgcacctgtg cttatttgga cccatcggaa     360

acagagcact ctgttctcaa acgcctcttc ctctcctttc tcgcttcccg ccatgacagg     420

ttcatccctc tgtttcgaag ctccttgtct gagatgtttg ttaagcttga agataaactt     480

tccgagaaaa agaagatcgc tgatttcaac tcgatcagcg attccatgtc gtttgattat     540

gttttccgtt tactctccga tggaacccct gattcgaaat tagctgctga gggacctgga     600

atgttcgatc tgtggcttgt gtttcaactc gccccattgg cttccattgg ccttcccaaa     660

attttctctg tttttgaaga tctcgtcatt cacaccattc ccctgccttt cttcccagtc     720

aagagtggtt acaggaagct ttatgaagcg ttttactcct cttctggctc atttctagac     780

gaagcagaga aacaggggat agacagggag aaagcatgtc acaatttagt gtttctcgct     840

ggattcaacg catacggggg aatgaaagtc ctttttccca ctttactgaa atgggtcggc     900
```

-continued

```
accgccggcg aggatctcca ccggaaactc gccgaggaag tcaggacaac cgtgaaggaa    960
gaagggggac tgactttctc cgccttggag aaaatgagtc tgctgaagtc cgtcgtgtac   1020
gaagcactca ggatcgaacc gccggtgccg ttccagtacg ggaaagcgaa ggaggatatc   1080
gtgattcaga gccacgattc ttctttcaag atcaaaaaag gggagacgat tttggttat    1140
cagccgtttg ctactaaaga tccgaagatt tttaaggatt cggagaagtt cgtgggcgat   1200
aggttcgtgg gagaagaagg ggagaagctt ttgaagtatg tttactggtc aaatgagcgg   1260
gagacagtgg agccgacgcg gangaacaag cagtgtccgg ggaagaatct ggtggtgctg   1320
ataggtagga ttatggtggt ggaattcttc cttcgttatg atacgttcac cgtggaggtc   1380
gcggatttgc cgctgggtcc ggcagtgaag ttcaagtcct taaccagagc aaccgatatg   1440
ttaaagctaa tgactaatta gttttatcat ttacagatag tgaattggtt gatgcacgga   1500
agctgtggcg gactgcgcac acatgattga gtacttgggg ttattaaagt aatttcgttg   1560
tgatccacgt ggtcttattt taatttgaga tctcattgtg tgttgtaacc caccggtcat   1620
cttattttat agtttgtttg ttttctcaat tatgctccaa attttaaaat aaataaatac   1680
catcttcttc ttttactaaa aaaaaaaaaa aaaaa                              1715
```